(12) United States Patent
Bold et al.

(10) Patent No.: US 6,706,731 B2
(45) Date of Patent: Mar. 16, 2004

(54) PYRIDINE DERIVATIVES INHIBITING ANGIOGENESIS AND/OR VEGF RECEPTOR TYROSINE KINASE

(75) Inventors: Guido Bold, Gipf-Oberfrick (CH); Paul William Manley, Arlesheim (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/203,579

(22) PCT Filed: Feb. 7, 2001

(86) PCT No.: PCT/EP01/01331
§ 371 (c)(1),
(2), (4) Date: Oct. 11, 2002

(87) PCT Pub. No.: WO01/58899
PCT Pub. Date: Aug. 16, 2001

(65) Prior Publication Data
US 2003/0158409 A1 Aug. 21, 2003

(30) Foreign Application Priority Data
Feb. 9, 2000 (CH) ................................. 265/00

(51) Int. Cl.[7] ...................... C07D 471/04; A61K 31/47; A61K 31/44
(52) U.S. Cl. ................... 514/307; 514/332; 546/148; 546/255
(58) Field of Search .............. 514/307, 332; 546/148, 255

(56) References Cited

U.S. PATENT DOCUMENTS 3,847,919 A * 11/1974 Knowles et al. ............ 544/247
5,654,307 A 8/1997 Bridges et al. ............. 514/258

FOREIGN PATENT DOCUMENTS

| WO | WO 97 34876 A | 9/1997 |
| WO | WO 98 13350 A | 4/1998 |
| WO | WO 98 13354 A | 4/1998 |
| WO | WO 98 35958 A | 8/1998 |

* cited by examiner

Primary Examiner—Zinna Northington Davis
(74) Attorney, Agent, or Firm—Lydia T. McNally; George R. Dohmann

(57) ABSTRACT

The invention relates to pyridine derivatives of formula I:

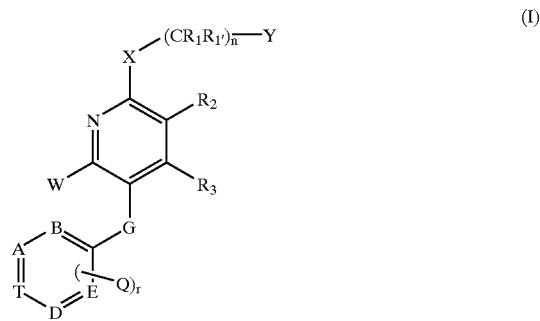

wherein the substituents and symbols are defined as indicated in the description, processes for the preparation thereof, their usage in the preparation of a pharmaceutical composition for the treatment of a disease which responds to an inhibition of angiogenesis, and pharmaceutical compositions containing such compounds.

20 Claims, No Drawings

PYRIDINE DERIVATIVES INHIBITING ANGIOGENESIS AND/OR VEGF RECEPTOR TYROSINE KINASE

The invention relates to new pyridine derivatives, processes for the preparation thereof, the application thereof in a process for the treatment of the human or animal body, the use thereof—alone or in combination with one or more other pharmaceutically active compounds—for the treatment of a disease, especially a proliferative disease, such as a tumour disease, a method for the treatment of such disease in mammals, especially in humans, and the use of such a compound—alone or in combination with one or more other pharmaceutically active compounds—for manufacture of a pharmaceutical preparation (medicament) for the treatment especially of a proliferative disease, such as a tumour.

Surprisingly, it has now been found that pyridine derivatives of formula I, described below, have advantageous pharmacological properties and inhibit, for example, the activity of the VEGF receptor tyrosine kinase and the VEGF-dependent cell proliferation.

The compounds of formula I permit, for example, an unexpected new therapeutic approach, especially for diseases in the treatment of which, and also for the prevention of which, an inhibition of angiogenesis and/or of the VEGF receptor tyrosine kinase shows beneficial effects.

The invention relates to compounds of formula I:

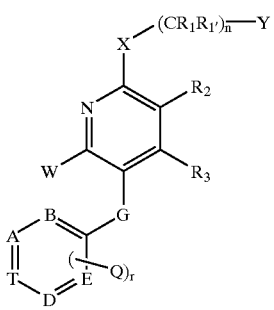

(I)

wherein

A, D and T, independently of one another, are each N, CH or $CR_4$, with the proviso that at least one of A and D is $CR_4$ when T is N;

$R_4$ is lower alkyl, lower alkenyl, lower alkylthio, mercapto, free, etherified or esterified hydroxy, unsubstituted, mono- or disubstituted amino or halogen;

B and E, independently of one another, are each N or CH;

G is $C_1$–$C_6$-alkylene, $C_2$–$C_6$-alkenylene, acyloxy- or hydroxy-substituted $C_1$–$C_6$-alkylene or $C_3$–$C_6$-alkenylene, $C_1$–$C_2$-alkyleneoxy, $C_1$–$C_2$-alkylenethio, $C_1$–$C_2$-alkyleneimino, —$CH_2$—O—$CH_2$—, —$CH_2$—S—$CH_2$—, —$CH_2$—NH—$CH_2$—, oxa, thia or imino;

n is 0 to 2;

Q is lower alkyl, whereby A, D and T are not substituted by Q if they represent $CR_4$;

r is 0 to 5;

$R_1$ und $R_{1'}$ independently of one another are each hydrogen or lower alkyl;

$R_2$ and $R_3$ a) independently of one another, are each lower alkyl; or b) together form a bridge of the part formula I*:

(I*)

wherein the ring members $T_1$, $T_2$, $T_3$ and $T_4$, independently of one another, are each nitrogen or CH, and binding is achieved via the atoms $T_1$ and $T_4$, the bonds characterised by a wavy line, independently of one another, are each either single or double bonds, m is 0 to 4 and Z is a substituent of one or more carbon atoms, whereby Z is unsubstituted, mono- or disubstituted amino, halogen, unsubstituted or substituted alkyl, free, etherified or esterified hydroxy, nitro, cyano, free or esterified carboxy, alkanoyl, unsubstituted, N-mono- or N,N-disubstituted carbamoyl, amidino, guanidino, mercapto, sulfo, phenylthio, phenyl lower alkylthio, alkylphenylthio, phenylsulfinyl, phenyl lower alkylsulfinyl, alkylphenylsulfinyl, phenylsulfonyl, phenyl lower alkylsulfonyl or alkylphenylsulfonyl, whereby if more than 1 radical Z is present (m≧2), the substituents Z are identical or different;

W is hydrogen, unsubstituted, mono- or disubstituted amino, halogen, unsubstituted or substituted alkyl, free, etherified or esterified hydroxy, nitro, cyano, free or esterified carboxy, alkanoyl, unsubstituted, N-mono- or N,N-disubstituted carbamoyl, amidino, guanidino, mercapto, sulfo, phenylthio, phenyl lower alkylthio, alkylphenylthio, phenylsulfinyl, phenyl lower alkylsulfinyl, alkylphenylsulfinyl, phenylsulfonyl, phenyl lower alkylsulfonyl or alkylphenylsulfonyl;

X is —N($R_5$)—, oxa, or thia; and $R_5$ is H or lower alkyl;

and Y is hydrogen, aryl, heterocyclyl or unsubstituted or substituted cycloalkyl;

or a tautomer of the said compound;

or an N-oxide of the said compound or tautomers thereof, whereby one or more N atoms carry an oxygen atom;

or a salt of the said compounds.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either unbranched or branched with single or multiple branching.

Where compounds of formula I are mentioned, this is taken to mean also the tautomers of the compounds of formula I.

Where the plural form is used for compounds, salts, and the like, this is taken to mean also a single compound, salt, or the like.

Asymmetric carbon atoms of a compound of formula I that are optionally present may exist in the (R), (S) or (R,S) configuration, preferably in the (R) or (S) configuration. Substituents at a double bond or a ring may be present in cis-(=Z-) or trans(=E-) form. The compounds may thus be present as mixtures of isomers or as pure isomers, preferably as enantiomer-pure diastereomers.

Of the ring members A, B, D, E and T in formula I, one ring member is preferably N, while the others are CH or $CR_4$. In particular, A, D or T is preferably N. If T is N, at least one of the ring members A or D is $CR_4$.

$R_4$ is preferably lower alkyl, especially methyl or ethyl; lower alkenyl, such as ethenyl or propenyl; lower alkylthio, such as methylthio or ethylthio; free etherified or esterified hydroxy as defined below; unsubstituted, mono- or disubstituted amino as defined below; or halogen, such as fluorine, chlorine, bromine or iodine. $R_4$ is most preferably methyl, hydroxy, methoxy or halogen.

If G is a bivalent group $C_1$–$C_2$-alkyleneoxy, $C_1$–$C_2$-alkylenethio or $C_1$–$C_2$-alkyleneimino, the alkylene group is bonded to the ring with the ring members A, B, D, E and T, while the hetero atom (O, S or NH) is bonded to the ring with the substituents $R_2$, $R_3$, W and X in formula I.

$C_1$–$C_6$-alkylene and $C_2$–$C_6$-alkenylene as G may be branched or preferably unbranched, and are in particular $C_1$–$C_4$-alkylene or $C_2$–$C_4$-alkenylene, primarily methylene (—$CH_3$—), ethylene (—$CH_2$—$CH_2$—), ethenylene (—CH=CH—), propylene (—$CH_2$—$CH_2$—$CH_2$—), propenylene (—CH=CH—$CH_2$—) or tetramethylene (—$CH_2$—$CH_2$—$CH_2$—$CH_2$—) and most preferably methylene, ethylene or ethenylene. In the definition of G, $C_1$–$C_2$-alkyleneoxy is —$CH_2$—O— or —$CH_2$—$CH_2$—O—, $C_1$–$C_2$-alkylenethio is —$CH_2$—S— or —$CH_2$—$CH_2$—S— and $C_1$–$C_2$-alkyleneimino is —$CH_2$—NH— or —$CH_2$—$CH_2$—NH—. G is most preferably methylene, ethylene or ethenylene. In $C_2$–$C_6$-alkenylene for G, the substituents are present on the double bond preferably in the E-(=trans-) form.

Acyloxy in acyloxy-substituted $C_1$–$C_6$-alkylene or $C_3$–$C_6$-alkenylene is preferably lower alkanoyloxy.

Hydroxy-substituted $C_1$–$C_6$-alkylene is preferably hydroxyethylene. Hydroxy-substituted $C_3$–$C_6$-alkenylene is preferably hydroxypropenylene.

The index n is preferably 0 or 1.

Lower alkyl is in particular $C_1$–$C_4$-alkyl, e.g. n-butyl, sec.-butyl, tert.-butyl, n-propyl, isopropyl or primarily methyl or also ethyl.

The index r is preferably 0 or 1.

Preferably, $R_2$ and $R_3$ together form a bridge of the part formula I*. Here, the index m is preferably 0, 1 or 2. In particular, m is preferably 0.

Preferably 0 or 1 of the ring members $T_1$, $T_2$, $T_3$ and $T_4$ is nitrogen and the remaining ring members are CH. Most preferably all of the ring members $T_1$, $T_2$, $T_3$ and $T_4$ are CH or $T_4$ is nitrogen and the remaining ring members $T_1$, $T_2$ and $T_3$ are CH.

Z and W, independently of one another, are preferably unsubstituted or substituted alkyl, as defined below; amino; hydroxy-lower alkylamino such as 2-hydroxyethylamino; lower alkanoylamino such as acetylamino; or halogen such as bromine; preferably only one substituent is present (m=1), especially one of the latter substituents, particularly halogen. A compound of formula I*, wherein Z is absent (m=0), is quite especially preferred. W stands especially preferred for hydrogen or lower alkyl, most preferably for hydrogen.

Mono- or disubstituted amino is especially amino substituted by one or two radicals selected independently of one another from lower alkyl, such as methyl; hydroxy-lower alkyl, such as 2-hydroxyethyl; phenyl; phenyl-lower alkyl; lower alkanoyl, such as acetyl; benzoyl; substituted benzoyl, wherein the phenyl radical is substituted especially by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group consisting of benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl or carbamoyl, or as an alternative or in addition to the above group of radicals, by aminocarbonylamino.

Halogen is primarily fluorine, chlorine, bromine, or iodine, especially fluorine, chlorine, or bromine.

Alkyl has preferably up to a maximum of 12 carbon atoms and is especially lower alkyl, especially methyl, or also ethyl, n-propyl, isopropyl, or tert-butyl.

Substituted alkyl is alkyl as last defined, especially lower alkyl, preferably methyl; where one or more, especially up to three, substituents may be present, primarily from the group selected from halogen, especially fluorine, and also from amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Etherified hydroxy is especially $C_8$–$C_{20}$-alkoxy, such as n-decyloxy, lower alkoxy (preferred), such as methoxy, ethoxy, isopropyloxy, or n-pentyloxy, phenyl-lower alkoxy, such as benzyloxy, or also phenyloxy, or as an alternative or in addition to the previous group, halogen-lower alkoxy, such as trifluoromethoxy or 1,1,2,2-tetrafluoroethoxy. Etherified hydroxy is most preferably methoxy or ethoxy.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl or ethoxycarbonyl, phenyl-lower alkoxycarbonyl, or phenyloxycarbonyl.

Alkanoyl is primarily alkyl-carbonyl, especially lower alkanoyl, e.g. acetyl.

N-mono- or N,N-disubstituted carbamoyl is especially substituted by one or two substituents, selected independently of one another from the group consisting of lower alkyl, phenyl-lower alkyl and hydroxy-lower alkyl, at the terminal nitrogen atom.

Alkylphenylthio is especially lower alkylphenylthio.

Alkylphenylsulfinyl is especially lower alkylphenylsulfinyl.

Alkylphenylsulfonyl is especially lower alkylphenylsulfonyl.

Oxa is —O—, thia is —S— and imino is —NH—.

Aryl is preferably an aromatic radical with 6 to 14 carbon atoms, especially phenyl, naphthyl, fluorenyl or phenanthrenyl, whereby the said radicals are unsubstituted or substituted by one or more substituents independently of one another, preferably up to three, primarily one or two substituents, especially those selected from unsubstituted, mono- or disubstituted amino, halogen, unsubstituted or substituted alkyl, free, etherified or esterified hydroxy, nitro, cyano, free or esterified carboxy, alkanoyl, unsubstituted, N-mono- or N,N-di-substituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkylsulfonyl, alkylphenylsulfonyl, lower alkenyl such as ethenyl, phenyl, lower alkylthio such as methylthio, lower alkanoyl such as acetyl, lower alkylmercapto such as methylmercapto (—S—$CH_3$), halogen-lower alkylmercapto such as trifluoromethylmercapto (—S—$CF_3$), lower alkylsulfonyl, halogen-lower alkylsulfonyl, such as in particular trifluoromethylsulfonyl, dihydroxybora [—$B(OH)_2$], heterocyclyl; and lower alkylenedioxy bound to adjacent carbon atoms of the ring, such as methylenedioxy; aryl is for example phenyl which is unsubstituted or is substituted by one or two substituents, independently of one another, selected from the group consisting of amino; lower alkanoylamino, especially acetylamino; halogen, especially fluorine, chlorine, bromine or iodine; lower alkyl, especially methyl or also ethyl, propyl or t.-butyl; halogen-lower alkyl, especially trifluoromethyl; hydroxy; lower alkoxy, especially methoxy or also ethoxy; phenyl-lower alkoxy, especially benzyloxy; and cyano, or (as an alternative or in addition to the above group of substituents) $C_8$–$C_{12}$-alkoxy, especially n-decyloxy, carbamoyl, lower alkylcarbamoyl, such as N-methyl- or N-tert.-butylcarbamoyl, lower alkanoyl such as acetyl, phenyloxy, halogen-lower alkoxy, such as trifluoromethoxy or 1,1,2,2-tetrafluoroethoxy, lower alkoxycarbonyl, such as ethoxycarbonyl, lower alkyl mercapto, such as methyl mercapto, halogen-lower alkylmercapto, such as trifluoromethylmercapto, hydroxy-lower alkyl, such as hydroxymethyl or 1-hydroxyethyl, lower alkylsulfonyl such as methylsulfonyl, halogen-lower alkylsulfonyl, such as trifluoromethylsulfonyl, phenylsulfonyl, dihydroxybora [—$B(OH)_2$], 2-methyl-pyrimidin-4-yl, oxazol-5-yl, 2-methyl-1,3-dioxolan-2-yl, 1H-pyrazol-3yl, 1-methyl-pyrazol-3-yl; and lower alkylenedioxy bound to two adjacent carbon atoms, such as methylenedioxy; especially preferred are one or two substituents selected independently of one another from lower alkyl, especially methyl, halogen, especially chlorine or bromine, and halogen-lower alkyl, especially trifluoromethyl. Aryl in the form of phenyl which is substituted by lower alkylene dioxy bound to two adjacent C-atoms, such as methylene dioxy, is preferably 3,4-methylene dioxyphenyl. In the cases where Y signifies aryl, aryl is most preferably phenyl which is preferably substituted by one or more substituents selected independently of one another from the group consisting of lower alkyl, especially methyl, ethyl, n-propyl, i-propyl or t-butyl; halogen, especially fluorine, chlorine, bromine or iodine; lower alkoxy, especially methoxy; and halogen-lower alkyl, especially trifluoromethyl; phenyl is most preferably substituted by one or two substituents selected independently of one another from the group consisting of lower alkyl, especially methyl, ethyl, isopropyl or t-butyl; halogen, especially bromine, chlorine or fluorine; and halogen-lower alkyl, especially trifluoromethyl.

Heterocyclyl is defined as below for heteroaryl, whereby the ring binding to the radical of the molecule of formula I can also be partially or wholly saturated. In the cases where Y signifies a partially or wholly saturated heterocyclic radical in the binding ring, Y is preferably an unsubstituted, or as for aryl, especially phenyl, a substituted, four- to eight-membered, especially six-membered, carbon ring which is preferably wholly saturated, and in which 1 to 4, especially 1 or 2, carbon atoms are replaced by hetero atoms selected from the group consisting of nitrogen, oxygen and sulfur, especially from the group consisting of oxygen and sulfur. In the cases where Y signifies a partially or wholly saturated heterocyclic radical in the binding ring, Y is most preferably unsubstituted cyclohexyl or cyclohexyl substituted by lower alkyl, in which two ring carbon atoms are replaced by oxygen.

Heteroaryl preferably signifies an unsaturated heterocyclic radical in the binding ring and is preferably mono- or also bi- or tricyclic, whereby, at least in the ring binding to the radical of the molecule of formula I, one or more, preferably one to four, especially one or two carbon atoms of a corresponding aryl radical are replaced by a hetero atom selected from the group consisting of nitrogen, oxygen and sulfur, whereby the binding ring has preferably 4 to 12, especially 5 to 7 ring atoms; whereby heteroaryl is unsubstituted or is substituted by one or more, especially 1 to 3, substituents selected independently from the group consisting of the above-mentioned substituents of aryl; and it is in particular a heteroaryl radical selected from the group consisting of imidazolyl, thienyl, furyl, pyranyl, thianthrenyl, isobenzofuranyl, benzofuranyl, chromenyl, 2H-pyrrolyl, pyrrolyl, lower alkyl substituted imidazolyl, benzimidazolyl, pyrazolyl, thiazolyl, isothiazolyl, oxazolyl, isoxazolyl, pyridyl, pyrazinyl, pyrimidinyl, pyridazinyl, indolizinyl, isoindolyl, 3H-indolyl, indolyl, indazolyl, triazolyl, tetrazolyl, purinyl, 4H-quinolizinyl, isoquinolyl, quinolyl, phthalazinyl, naphthyridinyl, quinoxalyl, quinazolinyl, cinnolinyl, pteridinyl, carbazolyl, phenanthridinyl, acridinyl, perimidinyl, phenanthrolinyl and furazanyl, whereby each of these radicals is bound by a ring to at least one hetero atom and the radical of the molecule of formula I; Isoquinolyl is preferred in particular. For cases where Y signifies isoquinolyl, isoquinolyl is most preferably 3-isoquinolyl.

Unsubstituted or substituted cycloalkyl is preferably $C_3$–$C_8$-cycloalkyl, which is unsubstituted or substituted in the same way as aryl, especially as defined for phenyl. Cyclohexyl or also cyclopentyl or cyclopropyl are preferred, particularly cyclohexyl.

The bonds in part formula I* characterized by wavy lines are present either as single or as double bonds. Preferably both are at the same time either single or double bonds. Most preferably, both are double bonds at the same time.

An N-oxide of a compound of formula I is preferably an N-oxide, in which a nitrogen in the ring with substituents G, $R_2$, $R_3$, W and X, a nitrogen in the ring formed by the part formula I*, or a nitrogen in the ring with the ring members A, B, D, E and T, carries an oxygen atom, or several of the said nitrogen atoms carry an oxygen atom.

Salts are especially the pharmaceutically acceptable salts of compounds of formula I (or an N-oxide thereof).

Such salts are formed, for example, as acid addition salts, preferably with organic or inorganic acids, from compounds of formula I (or an N-oxide thereof) with a basic nitrogen atom, especially the pharmaceutically acceptable salts. Suitable inorganic acids are, for example, hydrohalic acids, such as hydrochloric acid, sulphuric acid, or phosphoric acid.

Suitable organic acids are for example carboxylic, phosphonic, sulfonic or sulfonamic acids, e.g. acetic acid, propionic acid, octanoic acid, decanoic acid, dodecanoic acid, glycolic acid, lactic acid, 2-hydroxybutyric acid, gluconic acid, glucose monocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, maleic acid, hydroxymaleic acid, methylmaleic acid, cyclohexanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, glucuronic acid, galacturonic acid, methane- or ethane-sulfonic acid, 2-hydroxy-ethanesulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethyl-piperazine.

In the presence of a basic group and an acid group in the same molecule, a compound of formula I (or an N-oxide thereof) may also form internal salts.

For isolation or purification purposes it is also possible to use pharmaceutically unacceptable salts, for example picrates or perchlorates. Only the pharmaceutically acceptable salts or free compounds (if the occasion arises, in the form of pharmaceutical preparations) attain therapeutic use, and these are therefore preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

The compounds of formula I (or an N-oxide thereof) have valuable pharmacological properties, as described hereinbefore and hereinafter.

The efficacy of the compounds of the invention as inhibitors of VEGF-receptor tyrosine kinase activity can be demonstrated as follows:

Test for activity against VEGF-receptor tyrosine kinase: the test is conducted using Flt-1 VEGF-receptor tyrosine kinase. The detailed procedure is as follows: 30 µl kinase solution (kinase domain of Flt-1, Shibuya et al., Oncogene 5, 519–24 [1990], according to the specific activity, in order to achieve an activity of 4000–6000 counts per minute [cpm] in the sample without inhibitor) in 20 mM Tris.HCl pH 7.5, 3 mM manganese dichloride ($MnCl_2$), 3 mM magnesium chloride ($MgCl_2$) and 3 µg/ml poly(Glu,Tyr) 4:1 (Sigma, Buchs, Switzerland), 8 µM [$^{33}P$]-ATP (0.2 µCi/batch), 1% dimethyl sulfoxide, and 0 to 50 µM of the compound to be tested are incubated together for 10 minutes at room temperature. The reaction is then ended by the addition of 10 µl 0.25 M ethylenediaminetetraacetate (EDTA) pH 7. Using a multichannel dispenser (LAB SYSTEMS, USA), an aliquot of 20 µl is applied to a PVDF (=polyvinyl difluoride) Immobilon P membrane (Millipore, USA), which is incorporated into a Millipore microtitre filter manifold, and connected to a vacuum. Following complete elimination of the liquid, the membrane is washed 4 times successively in a bath containing 0.5% phosphoric acid ($H_3PO_4$), incubated for 10 minutes each time while shaking, then mounted in a Hewlett Packard TopCount Manifold and the radioactivity measured after the addition of 10 µl Microscint® (β-scintillation counter liquid; Packard USA). $IC_{50}$-values are determined by linear regression analysis of the percentages for the inhibition of each compound in three concentrations (as a rule 0.01, 0.1, and 1 µM). Inhibition values ($IC_{50}$ 50% inhibition of activity compared with the control without an inhibitor of formula I) in the range of 5 nM to 1 µM, especially in the range of 5 nM to 500 nM are found.

Analogously to the above test, the efficacy of the compounds according to the invention as inhibitors of VEGF activity can be tested using the VEGF receptor tyrokinase KDR. In this test, instead of the Flt-1 kinase domain, the KDR kinase domain (Parast et al., Biochemistry 37 (47), 16788–801 (1998)) is used. The only difference in carrying out this test from the above test lies in the concentration of poly(Glu,Tyr) 4:1 (8 µg/ml), $MnCl_2$ (1 mM) and $MgCl_2$ (10 mM). Compounds of formula I in this instance have $IC_{50}$ values in the range of 0.5 nM to 1 µM, especially in the range of 0.5 nM to 200 nM.

The antitumour efficacy of the compounds of the invention can be demonstrated in vivo as follows:

In vivo activity in the nude mouse xenotransplant model: female BALB/c nude mice (8–12 weeks old, Novartis Animal Farm, Sissein, Switzerland) are kept under sterile conditions with water and feed ad libitum. Tumours are induced by subcutaneous injection of tumour cells (human epithelial cell line A-431; American Type Culture Collection (ATCC), Rockville, Md., USA, Catalogue Number ATCC CRL 1555; cell line from an 85-year-old woman; epidermoid carcinoma cell line) into carrier mice. The resulting tumours pass through at least three consecutive transplantations before the start of treatment. Tumour fragments (about 25 mg) are implanted subcutaneously in the left flank of the animals using a 13-gauge trocar needle under Forene® anaesthesia (Abbott, Switzerland). Treatment with the test compound is started as soon as the tumour has reached a mean volume of 100 $mm^3$. Tumour growth is measured two to three times a week and 24 hours after the last treatment by determining the length of two perpendicular axes. The tumour volumes are calculated in accordance with published methods (see Evans et al., Brit. J. Cancer 45, 466–8 [1982]). The antitumour efficacy is determined as the mean increase in tumour volume of the treated animals divided by the mean increase in tumour volume of the untreated animals (controls) and, after multiplication by 100, is expressed as T/C %. Tumour regression (given in %) is reported as the smallest mean tumour volume in relation to the mean tumour volume at the start of treatment. The test compound is administered daily by gavage.

As an alternative to cell line A-431, other cell lines may also be used in the same manner, for example:

the MCF-7 breast adenocarcinoma cell line (ATCC No. HTB 22; see also J. Natl. Cancer Inst. (Bethesda) 51, 1409–16 (1973));

the MDA-MB 468 breast adenocarcinoma cell line (ATCC No. HTB 132; see also In Vitro 14, 911–15 [1978]);

the MDA-MB 231 breast adenocarcinoma cell line (ATCC No. HTB 26; see also J. Natl. Cancer Inst. (Bethesda) 53, 661–74 (1974));

the Colo 205 colon carcinoma cell line (ATCC No. CCL 222; see also Cancer Res. 38, 1345–55 [1978]);

the HCT 116 colon carcinoma cell line (ATCC No. CCL 247; see also Cancer Res. 41, 1751–6 [1981]);

the DU145 prostate carcinoma cell line DU 145 (ATCC No. HTB 81; see also Cancer Res. 37, 4049–58 [1978]); and the PC-3 prostate carcinoma cell line PC-3 (ATCC No. CRL 1435; see also Cancer Res. 40, 524–34 [1980]).

Using a further cellular in vitro experiment, the inhibition of the VEGF-induced KDR autophosphorylation can be confirmed: Transfected CHO cells, which permanently express human VEGF receptor (KDR), are seeded in culture medium (with 10% fetal calf serum=FCS) in 6-well cell culture plates and incubated at 37° C., 5% $CO_2$ until they are approximately 80% confluent. The compounds to be tested are then diluted in culture medium (without FCS, with 0.1% bovine serum albumin=BSA) and added to the cells. (Controls receive medium without test compounds). After incubation for two hours at 37° C., recombinant VEGF is added; the final VEGF concentration is 20 ng/ml. After incubating for a further five minutes at 37° C., the cells are washed twice with ice-cold PBS (phosphate-buffered physiological saline) and immediately lysed in 100 µl lysis buffer per well. The lysates are then centrifuged to remove the cell nuclei, and the protein concentrations of the supernatants are determined by a commercial protein assay (BIORAD). The lysates can then be either further used immediately or stored at −20° C. if required.

To determine the KDR phosphorylation, a "sandwich ELISA" is carried out. A monoclonal antibody to KDR (for example Mab 1495.12.14; prepared by H. Towbin) is immobilised on black ELISA plates (OptiPlate™ HTRF-96 by Packard). Subsequently, the plates are washed and any remaining free protein binding sites are neutralised with 1% BSA in PBS. The cell lysates (20 µg protein per well) are then incubated over night at 4° C. together with an anti-phosphotyrosine antibody, which is coupled with alkaline phosphatase (PY20:AP from Transduction Laboratories). Binding of the anti-phosphotyrosine antibody is then demonstrated with a luminescing AP substrate (CDP-Star Ready to use with Emerald II; TROPIX). Luminescence is measured in a Packard Top Count Microplate Scintillation Counter (Top Count). The difference between the signal from the positive control (stimulated with VEGF) and that from the negative control (not stimulated with VEGF) corresponds to the VEGF-induced KDR phosphorylation (=100%). The activity of the tested substances is calculated as % inhibition of the VEGF-induced KDR phosphorylation, whereby the concentration of a substance which effects semi-maximum inhibition is called $ED_{50}$ (effective dose for 50% inhibition). Compounds of formula I in this instance have $ED_{50}$ values in the range of 0.5 nM to 1 µM, especially 0.5 nM to 100 nM.

A compound of formula I, or N-oxide thereof, inhibits to varying degrees also other tyrosine kinases involved in signal transduction which are mediated by trophic factors, for example abl kinase, kinases from the src family, especially c-src kinase, lck, and fyn; or in a broader sense kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase, especially Flt-1, KDR and Flk; or in a broader sense also serine/threonine kinases, all of which play a role in growth regulation and transformation in mammalian cells, including human cells.

The inhibition of c-erbB2 tyrosine kinase (HER-2) can be measured, for example, in the same way as the inhibition of EGF-R protein kinase (see House et al., Europ. J. Biochem. 140, 363–7 [1984]). The erbB2 kinase can be isolated, and its activity determined, using methods known per se (see T. Akiyama et al., Science 232, 1644 [1986]).

An inhibitory effect can also be found especially on PDGF-receptor kinase, which is determined according to the method described by Trinks et al. [see J. Med. Chem. 37(7):1015–27 (1994)].

In order to evaluate the potential of the compounds of formula I for clinical drug-drug interactions, their potential to inhibit cytochromes P450 (CYPs) is tested. Cytochromes P450 are the principal, hepatic xenobiotic metabolizing enzymes. In general it can be said that the less a compound inhibits cytochromes P450, the less potential this compound has for clinical drug-drug interactions. The potential for enzyme inhibition is routinely assessed by performing in vitro inhibition studies using cDNA-expressed enzymes or human liver microsomes (Parkinson, A., Toxicol. Pathol. 24, 45–57 [1996]). Herein, a microtiter plate-based, fluorometric assay according to Crespi et al., Anal. Biochem. 248, 188–190 (1997) is used to determine the 50% inhibition concentration ($IC_{50}$) of a compound of formula I for the principal drug-metabolizing enzymes CYP1A2, CYP2C8, CYP2C9, CYP2C19, CYP2D6 and CYP3A4.

Compounds of formula I, wherein one or more of A, B, D, E and T, especially of A, D and T represent substituted ring carbon or ring nitrogen atoms including N-oxides, and tautomers of such compounds exhibit a higher $IC_{50}$ value for the inhibition of cytochromes P450 compared to other compounds of formula I and are therefore preferred. Most preferred in this context are compounds of formula I, wherein one or more, especially one, of A, D and T independently of one another represent a lower alkyl-, lower alkoxy-, halogen- or, especially, hydroxy-substituted ring carbon atom or a ring nitrogen atom carrying an oxygen atom.

On the basis of these studies, a compound of formula I (or an N-oxide thereof) according to the invention shows therapeutic efficacy especially against disorders dependent on protein kinase, especially proliferative diseases.

Owing to their efficacy as inhibitors of VEGF-receptor tyrosine kinase activity, the compounds according to the invention inhibit in particular the growth of vessels and are therefore effective for example against a number of diseases associated with deregulated angiogenesis, for example diseases caused by ocular neovascularisation, especially retinopathies, primarily diabetic retinopathy or age-induced macular degeneration; psoriasis; haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various imflammatory diseases, such as arthritis, especially rheumatoid arthritis, arterial arteriosclerosis and that occurring after transplants, endometriosis or chronic asthma; and especially neoplastic diseases (solid tumours and liquid tumours), such as especially breast cancer, cancer of the colon, lung cancer (especially small-cell lung cancer), or cancer of the prostate. The compounds of formula I (or N-oxides thereof) inhibit the growth of tumours and are especially suited to preventing the metastatic spread of tumours and the growth of micrometastases.

A compound of formula I (or an N-oxide thereof) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I (or an N-oxide thereof) can besides or in addition be administered for tumour therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour remission, or even chemopreventive therapy, for example in patients at risk.

Therapeutic agents for possible combination are especially one or more antiproliferative, cytostatic or cytotoxic compounds, for example a chemotherapeutic agent or several selected from the group comprising an inhibitor of polyamine biosynthesis, an inhibitor of protein kinase, especially of serine/threonine protein kinase, such as protein kinase C, or of tyrosine protein kinase, such as epidermal growth factor receptor protein tyrosine kinase, a cytokine, a negative growth regulator, such as TGF-β or IFN-β, an aromatase inhibitor, and a classical cytostatic.

Compounds according to the invention are not only for the (prophylactic and preferably therapeutic) treatment of humans, but also for the treatment of other warm-blooded animals, for example of commercially useful animals, for example rodents, such as mice, rabbits or rats, or guinea-pigs. They may also be used as a reference standard in the test systems described above to permit-a comparison with other compounds.

In general, the invention relates also to the use of a compound of formula I (or an N-oxide thereof) for the inhibition of VEGF-receptor tyrosine kinase activity.

A compound of formula I (or an N-oxide thereof) may also be used for diagnostic purposes, for example with tumours that have been obtained from warm-blooded animal "hosts", especially humans, and implanted into mice to test them for decreases in growth after treatment with such a compound, in order to investigate their sensitivity to the said compound and thus to improve the detection and determination of possible therapeutic methods for neoplastic diseases in the original host.

With the groups of preferred compounds of formula I mentioned hereinafter, definitions of substituents from the general definitions mentioned hereinbefore may reasonably be used, for example, to replace more general definitions with more specific definitions or especially with definitions characterised as being preferred.

Preference is given to a compound of formula I wherein

A, D and T, independently of one another, are each N, CH or $CR_4$, with the proviso that A or D is $CR_4$ when T is N;

$R_4$ is lower alkyl, lower alkenyl, lower alkylthio, mercapto, free, etherified or esterified hydroxy, unsubstituted, mono- or disubstituted amino or halogen;

B and E, independently of one another, are each N or CH;

G is $C_1$–$C_6$-alkylene, $C_2$–$C_6$-alkenylene, acyloxy- or hydroxy-substituted $C_1$–$C_6$-alkylene or $C_3$–$C_6$-alkenylene, $C_1$–$C_2$-alkyleneoxy, $C_1$–$C_2$-alkylenethio, $C_1$–$C_2$-alkyleneimino, —$CH_2$—O—$CH_2$—, —$CH_2$—S—$CH_2$—, —$CH_2$—NH—$CH_2$—, oxa, thia or imino;

n is 0 to 2;

Q is lower alkyl, whereby A, D and T are not substituted by Q if they represent $CR_4$;

r is 0 to 5;

$R_1$ und $R_{1'}$ independently of one another are each hydrogen or lower alkyl;

$R_2$ and $R_3$ a) independently of one another, are each lower alkyl; or b) together form a bridge of part formula I*, wherein the ring members $T_1$, $T_2$, $T_3$ and $T_4$, independently of one another, are each nitrogen or CH, and binding is achieved via the atoms $T_1$ and $T_4$, the bonds characterised by a wavy line, independently of one another, are each either single or double bonds, m is 0 to 4 and Z is a substituent of one or more carbon atoms, whereby Z is unsubstituted, mono- or disubstituted amino, halogen, unsubstituted or substituted alkyl, free, etherified or esterified hydroxy, nitro, cyano, free or esterified carboxy, alkanoyl, unsubstituted, N-mono- or N,N-disubstituted carbamoyl, amidino, guanidino, mercapto, sulfo, phenylthio, phenyl lower alkylthio, alkylphenylthio, phenylsulfinyl, phenyl lower alkylsulfinyl, alkylphenylsulfinyl, phenylsulfonyl, phenyl lower alkylsulfonyl or alkylphenylsulfonyl, whereby if more than 1 radical Z is present (m≧2), the substituents Z are identical or different;

W is hydrogen, unsubstituted, mono- or disubstituted amino, halogen, unsubstituted or substituted alkyl, free, etherified or esterified hydroxy, nitro, cyano, free or esterified carboxy, alkanoyl, unsubstituted, N-mono- or N,N-disubstituted carbamoyl, amidino, guanidino, mercapto, sulfo, phenylthio, phenyl lower alkylthio, alkylphenylthio, phenylsulfinyl, phenyl lower alkylsulfinyl, alkylphenylsulfinyl, phenylsulfonyl, phenyl lower alkylsulfonyl or alkylphenylsulfonyl;

X is —N($R_5$)—, oxa, or thia; and $R_5$ is H or lower alkyl;

and Y is hydrogen, aryl, heteroaryl or unsubstituted or substituted cycloalkyl;

or a tautomer of the said compound;

or an N-oxide of the said compound or tautomers thereof, whereby one or more N atoms carry an oxygen atom;

or a salt of the said compounds.

Preference is also given to a compound of formula I wherein

A, D and T, independently of one another, are each N, CH or $CR_4$, with the proviso that A or D is $CR_4$ when T is N;

$R_4$ is lower alkyl, lower alkenyl, lower alkylthio, mercapto, hydroxy, lower alkoxy, phenyl lower alkoxy, phenyloxy, halogen lower alkoxy, lower alkanoyloxy, lower alkoxycarbonyloxy, phenyl lower alkoxycarbonyloxy, amino, N-lower alkylamino, hydroxy lower alkylamino, lower alkanoylamino, phenyl lower alkylamino, N,N-di-lower alkylamino oder halogen;

B and E, independently of one another, are each N or CH;

G is $C_1$–$C_6$-alkylene, $C_2$–$C_6$-alkenylene; $C_1$–$C_6$-alkylene or $C_3$–$C_6$-alkenylene substituted by hydroxy or by lower alkanoyloxy; $C_1$–$C_2$-alkyleneoxy, $C_1$–$C_2$-alkylenethio, $C_1$–$C_2$-alkyleneimino, —$CH_2$—O—$CH_2$—, —$CH_2$—S—$CH_2$—, —$CH_2$—NH—$CH_2$—, oxa, thia or imino, with the proviso that if G is a bivalent group $C_1$–$C_2$-alkyleneoxy, $C_1$–$C_2$-alkylenethio or $C_1$–$C_2$-alkyleneimino, the alkylene group is bonded to the ring with the ring members A, B, D, E and T, while the hetero atom is bonded to the ring with the substituents $R_2$, $R_3$, W and X;

n is 0 to 2;

Q is lower alkyl, whereby A, D and T are not substituted by Q if they represent $CR_4$;

r is 0 to 5;

$R_1$ und $R_{1'}$ independently of one another are each hydrogen or lower alkyl;

$R_2$ and $R_3$ a) independently of one another, are each lower alkyl; or b) together form a bridge of part formula I*, wherein at most two of the ring members $T_1$, $T_2$, $T_3$ and $T_4$ are nitrogen, and the others are CH, and binding is achieved via the atoms $T_1$ and $T_4$, the bonds characterised by a wavy line, independently of one another, are each either single or double bonds, m is 0 to 4 and Z is a substituent of one or more carbon atoms, whereby Z is lower alkyl, amino, N-lower alkylamino, hydroxy lower alkylamino, lower alkanoylamino, N,N-di-lower alkylamino, halogen, halogen lower alkyl, hydroxy, lower alkoxy, halogen lower alkoxy, lower alkanoyloxy, lower alkoxycarbonyloxy, nitro, cyano, carboxy, lower alkoxycarbonyl, lower alkanoyl, carbamoyl; carbamoyl substituted on nitrogen by one or two substituents selected independently of one another from the group consisting of lower alkyl and hydroxy lower alkyl; amidino, guanidine, mercapto or sulfo, whereby if more than one radical Z is present (m≧2), the substituents Z are identical or different;

W is hydrogen, lower alkyl, amino, N-lower alkylamino, hydroxy lower alkylamino, lower alkanoylamino, N,N-di-lower alkylamino, halogen, halogen lower alkyl, hydroxy, lower alkoxy, halogen lower alkoxy, lower alkanoyloxy, lower alkoxycarbonyloxy, nitro, cyano, carboxy, lower alkoxycarbonyl, lower alkanoyl, carbamoyl; carbamoyl substituted on nitrogen by one or two substituents selected independently of one another from the group consisting of lower alkyl and hydroxy lower alkyl; amidino, guanidino, mercapto or sulfo;

X is —N($R_5$)—, oxa, or thia; and $R_5$ is H or lower alkyl;

and Y is unsubstituted or substituted cyclohexyl, isoquinolyl or unsubstituted or substituted phenyl, whereby substituted cyclohexyl and substituted phenyl are substituted by one or more substituents selected independently of one another from the group consisting of lower alkyl, lower alkoxy, halogen and halogen lower alkyl;

or a tautomer of the said compound;

or an N-oxide of the said compound or tautomers thereof, whereby one or more N atoms carry an oxygen atom;

or a salt of the said compounds.

In addition, preference is given to a compound of formula I wherein

A or D is N, while the other is CH, and T is CH or $CR_4$; or

A or D is CH, while the other is $CR_4$, and T is N;

$R_4$ is lower alkyl, lower alkenyl, lower alkylthio, mercapto, hydroxy, lower alkoxy, halogen lower alkoxy, lower alkanoyloxy, lower alkoxycarbonyloxy, amino, N-lower alkylamino, hydroxy lower alkylamino, lower alkanoylamino, N,N-di- lower alkylamino oder halogen;

B and E are CH;

G is $C_1$–$C_6$-alkylene, $C_2$–$C_6$-alkenylene; $C_1$–$C_6$-alkylene or $C_3$–$C_6$-alkenylene substituted by hydroxy or by lower alkanoyloxy; $C_1$–$C_2$-alkyleneoxy, $C_1$–$C_2$-alkylenethio, $C_1$–$C_2$-alkyleneimino, —$CH_2$—O—$CH_2$—, —$CH_2$—S—$CH_2$—, —$CH_2$—NH—$CH_2$—, oxa, thia or imino, with the proviso that if G is a bivalent group $C_1$–$C_2$-alkyleneoxy, $C_1$–$C_2$-alkylenethio or $C_1$–$C_2$-alkyleneimino, the alkylene group is bonded to the ring with the ring members A, B, D, E and T, while the hetero atom is bonded to the ring with the substituents $R_2$, $R_3$, W and X;

n is 0 to 2;

Q is lower alkyl, whereby A, D and T are not substituted by Q if they represent $CR_4$;

r is 0 or 1;

$R_1$ und $R_{1'}$ independently of one another are each hydrogen or lower alkyl;

$R_2$ and $R_3$ together form a bridge of part formula I*, wherein the ring members $T_1$, $T_2$, $T_3$ and $T_4$ are CH, and binding is achieved via the atoms $T_1$ and $T_4$, the bonds characterised by a wavy line are double bonds, m is 0 to 2 and Z is a substituent of one or more carbon atoms, whereby Z is lower alkyl, amino, N-lower alkylamino, hydroxy lower alkylamino, lower alkanoylamino, N,N-di-lower alkylamino, halogen, halogen lower alkyl, hydroxy, lower alkoxy, halogen lower alkoxy, lower alkanoyloxy, lower alkoxycarbonyloxy, nitro, cyano, carboxy, lower alkoxycarbonyl, lower alkanoyl, carbamoyl; carbamoyl substituted on nitrogen by one or two substituents selected independently of one another from the group consisting of lower alkyl and hydroxy lower alkyl; amidino, guanidino, mercapto or sulfo, whereby if more than one radical Z is present (m=2), the substituents Z are identical or different;

W is hydrogen, lower alkyl, amino, N-lower alkylamino, hydroxy lower alkylamino, lower alkanoylamino, N,N-di-lower alkylamino, halogen, halogen lower alkyl, hydroxy, lower alkoxy, halogen lower alkoxy, lower alkanoyloxy, lower alkoxycarbonyloxy, nitro, cyano, carboxy, lower alkoxycarbonyl, lower alkanoyl, carbamoyl; carbamoyl substituted on nitrogen by one or two substituents selected independently of one another from the group consisting of lower alkyl and hydroxy lower alkyl; amidino, guanidino, mercapto or sulfo;

X is —N($R_5$)—, oxa, or thia; and $R_5$ is H or lower alkyl;

and Y is unsubstituted or substituted cyclohexyl, isoquinolyl or unsubstituted or substituted phenyl, whereby substituted cyclohexyl and substituted phenyl are substituted by one or more substituents selected independently of one another from the group consisting of lower alkyl, lower alkoxy, halogen and halogen lower alkyl;

or a tautomer of the said compound;

or an N-oxide of the said compound or tautomers thereof, whereby one or more N atoms carry an oxygen atom;

or a salt of the said compounds.

Equally preferred is a compound of formula I wherein

A or D is N, while the other is CH, and T is CH or $CR_4$; or

A or D is CH, while the other is $CR_4$, and T is N;

$R_4$ is lower alkyl, hydroxy, lower alkoxy or halogen;

B and E are CH;

G is $C_1$–$C_6$-alkylene, $C_2$–$C_6$-alkenylene; $C_1$–$C_6$-alkylene or $C_3$–$C_6$-alkenylene substituted by hydroxy or by lower alkanoyloxy; $C_1$–$C_2$-alkyleneoxy, $C_1$–$C_2$-alkylenethio, $C_1$–$C_2$-alkyleneimino, —$CH_2$—O—$CH_2$—, —$CH_2$—S—$CH_2$—, —$CH_2$—NH—$CH_2$—, oxa, thia or imino, with the proviso that if G is a bivalent group $C_1$–$C_2$-alkyleneoxy, $C_1$–$C_2$-alkylenethio or $C_1$–$C_2$-alkyleneimino, the alkylene group is bonded to the ring with the ring members A, B, D, E and T, while the hetero atom is bonded to the ring with the substituents $R_2$, $R_3$, W and X;

n is 0 to 2;

r is 0;

$R_1$ und $R_1'$ independently of one another are each hydrogen or lower alkyl;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds characterised by a wavy line are double bonds, and m is 0;

W stands for hydrogen or lower alkyl;

X is —N($R_5$)—, oxa, or thia; and $R_5$ is H or lower alkyl;

and Y is substituted cyclohexyl, isoquinolyl or unsubstituted or substituted phenyl, whereby substituted cyclohexyl and substituted phenyl are substituted by one to three substituents selected independently of one another from the group consisting of lower alkyl, lower alkoxy, halogen and halogen lower alkyl;

or a tautomer of the said compound;

or an N-oxide of the said compound or tautomers thereof, whereby one or more N atoms carry an oxygen atom;

or a salt of the said compounds.

In addition, a compound of formula I is preferred, wherein

A or D is N, while the other is CH, and T is CH or $CR_4$; or

A or D is CH, while the other is $CR_4$, and T is N;

$R_4$ is lower alkyl, hydroxy, lower alkoxy or halogen;

B and E are CH;

G is $C_1$–$C_6$-alkylene or $C_2$–$C_6$-alkenylene;

n is 0 or 1;

r is 0;

$R_1$ und $R_1'$ independently of one another are each hydrogen or lower alkyl;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds characterised by a wavy line are double bonds, and m is 0;

W stands for hydrogen or lower alkyl;

X is —N($R_5$)—; and $R_5$ is H or lower alkyl;

and Y is substituted cyclohexyl, isoquinolyl or unsubstituted or substituted phenyl, whereby substituted cyclohexyl and substituted phenyl are substituted by one to three substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

Equally preferred is a compound of formula I wherein

A or D is N, while the other is CH, and T is CH or $CR_4$; or

A or D is CH, while the other is $CR_4$, and T is N;

$R_4$ is methyl, hydroxy or methoxy;

B and E are CH;

G is methylene, ethylene or ethenylene;

n is 0;

r is 0;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds characterised by a wavy line are double bonds, and m is 0;

W is hydrogen;

X is —N($R_5$)—; and $R_5$ is H;

and Y is substituted cyclohexyl, isoquinolyl or unsubstituted or substituted phenyl, whereby substituted cyclohexyl and substituted phenyl are substituted by one or two substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

Also preferred is a compound of formula I, wherein

A or D is N, while the other is CH, and T is CH or $CR_4$; or

A or D is CH, while the other is $CR_4$, and T is N;

$R_4$ is methyl, hydroxy or methoxy;

B and E are CH;

G is methylene, ethylene or ethenylene;

n is 0;

r is 0;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds characterised by a wavy line are double bonds, and m is 0;

W is hydrogen;

X is —N($R_5$)—; and $R_5$ is H;

and Y is substituted cyclohexyl, isoquinolyl or unsubstituted or substituted phenyl, whereby substituted cyclohexyl is substituted by one or two independent substituents lower alkyl and substituted phenyl is substituted by one or two substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

Furthermore, a compound of formula I is preferred, wherein

A or D is N, while the other is CH, and T is CH or $CR_4$;

$R_4$ is methyl, hydroxy, methoxy or halogen;

B and E are CH;

G is methylene, ethylene or ethenylene;

n is 0;

r is 0;

$R_2$ and $R_3$ together form a bridge of part formula I*, in which 0 to 2 of the ring members $T_1$, $T_2$, $T_3$ and $T_4$ are nitrogen and the remaining ring members are CH, and binding is achieved via the atoms $T_1$ and $T_4$, the bonds characterised by a wavy line are double bonds, and m is 0;

W stands for hydrogen or lower alkyl;

X is —N($R_5$)—; and $R_5$ is H;

and Y is substituted cyclohexyl, isoquinolyl or unsubstituted or substituted phenyl, whereby substituted cyclohexyl and substituted phenyl are substituted by one or two substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

Furthermore, a compound of formula I is also preferred, wherein

A or D is N, while the other is CH, and T is CH or $CR_4$;

$R_4$ is methyl, hydroxy or methoxy;

B and E are CH;

G is methylene, ethylene or ethenylene;

n is 0;

r is 0;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds characterised by a wavy line are double bonds, and m is 0;

W is hydrogen;

X is —N($R_5$)—; and $R_5$ is H;

and Y is substituted cyclohexyl, isoquinolyl or unsubstituted or substituted phenyl, whereby substituted cyclohexyl and substituted phenyl are substituted by one or two substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

A further especially preferred embodiment of the invention relates to a compound of formula I, wherein A or D is CH, while the other is $CR_4$, and T is N;

$R_4$ is methyl, hydroxy, methoxy or halogen;

B and E are CH;

G is methylene, ethylene or ethenylene;

n is 0;

r is 0;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds characterised by a wavy line are double bonds, and m is 0;

W is hydrogen;

X is —N($R_5$)—; and $R_5$ is H;

and Y is substituted cyclohexyl, isoquinolyl or unsubstituted or substituted phenyl, whereby substituted cyclohexyl and substituted phenyl are substituted by one or two substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

A further especially preferred embodiment of the invention also relates to a compound of formula I, wherein A or D is CH, while the other is $CR_4$, and T is N;

$R_4$ is methyl, hydroxy or methoxy;

B and E are CH;

G is methylene, ethylene or ethenylene;

n is 0;

r is 0;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds characterised by a wavy line are double bonds, and m is 0;

W is hydrogen;

X is —N($R_5$)—; and $R_5$ is H;

and Y is substituted cyclohexyl, isoquinolyl or unsubstituted or substituted phenyl, whereby substituted cyclohexyl and substituted phenyl are substituted by one or two substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

Special preference is given to a compound of formula I, such as is mentioned in the examples below, or a pharmaceutically acceptable salt thereof, especially a compound specifically mentioned in the examples or a salt thereof.

Also especially preferred are all compounds of formula I, which in the test according to Example 51 have an $ED_{50}$ value of less than 1 $\mu$M, most preferably those having an $ED_{50}$ value of less than 100 nM.

Very preferred is the compound with the designation 1-[4-(tert-butyl)-anilino]-4-[2-(pyridin-3-yl)-ethyl]-isoquinoline, wherein, based on formula I the symbols have the following significances: $R_2$ and $R_3$ together form a bridge of the part formula I*; $T_1=T_2=T_3=T_4=$CH; r=n=m=0; A=N; B=D=E=T=CH; W=H; G=$CH_2$—$CH_2$; X=NH; Y=4-(tert-butyl)-phenyl; or a salt thereof.

Likewise very preferred is the compound with the designation 1-(4-isopropyl-3-methylanilino)-4-[2-(pyridin-3-yl)-ethyl]-isoquinoline, wherein, based on formula I, the symbols have the following significances: $R_2$ and $R_3$ together form a bridge of the part formula I*; $T_1=T_2=T_3=T_4=$CH; r=n=m=0; A=N; B=D=E=T=CH; W=H; G=$CH_2$—$CH_2$; X=NH; Y=4-isopropyl-3-methylphenyl; or a salt thereof.

Also very preferred is the compound with the designation 1-(3-bromo-4-ethylanilino)-4-[2-(pyridin-3-yl)-ethyl]-isoquinoline, wherein, based on formula I, the symbols have the following significances: $R_2$ and $R_3$ together form a bridge of the part formula I*; $T_1=T_2=T_3=T_4=$CH; r=n=m=0; A=N; B=D=E=T=CH; W=H; G=$CH_2$—$CH_2$; X=NH; Y=3-bromo-4-ethylphenyl; or a salt thereof.

Also very preferred is the compound with the designation 1-[4-(tert-butyl)-anilino]-4-[(6-hydroxy-pyridin-3-yl)- methyl]-isoquinoline, wherein, based on formula 1, the symbols have the following significances: $R_2$ and $R_3$ together form a bridge of the part formula I*; $T_1=T_2=T_3=T_4=CH$; r=n=m=0; A=N; B=D=E=CH; $T=CR_4$; $R_4=OH$; W=H; $G=CH_2$; X=NH; Y=4-(tert-butyl)-phenyl; or a salt thereof.

Also very preferred is the compound with the designation 5-[4-(tert-butyl)-anilino]-8-[(6-hydroxy-pyridin-3-yl)-methyl]-[1,6]naphthyridine, wherein, based on formula the symbols have the following significances: $R_2$ and $R_3$ together form a bridge of the part formula I*; $T_1=T_2=T_3=CH$; $T_4=N$; r=n=m=0; A=N; B=D=E=CH; $T=CR_4$; $R_4=OH$; W=H; $G=CH_2$; X=NH; Y=4-(tert-butyl)-phenyl; or a salt thereof.

Also very preferred is the compound with the designation 1-[4-(tert-butyl)-anilino]-4-[(6-methoxy-pyridin-3-yl)-methyl]-isoquinoline, wherein, based on formula I, the symbols have the following significances: $R_2$ and $R_3$ together form a bridge of the part formula I*; $T_1=T_2=T_3=T_4=CH$; r=n=m=0; A=N; B=D=E=CH; $T=CR_4$; $R_4=O$—$CH_3$; W=H; $G=CH_2$; X=NH; Y=4-(tert-butyl)-phenyl; or a salt thereof.

Also very preferred is the compound with the designation 1-(3-bromo-4-ethylanilino)-4-[(6-hydroxy-pyridin-3-yl)-methyl]-isoquinoline, wherein, based on formula I, the symbols have the following significances: $R_2$ and $R_3$ together form a bridge of the part formula I*; $T_1=T_2=T_3=T_4=CH$; r=n=m=0; A=N; B=D=E=CH; $T=CR_4$; $R_4=OH$; W=H; $G=CH_2$; X=NH; Y=3-bromo-4-ethylphenyl; or a salt thereof.

Also very preferred is the compound with the designation 5-[4-(tert-butyl)-anilino]-8-[(6-methoxy-pyridin-3-yl)-methyl]-[1,6]naphthyridine, wherein, based on formula I, the symbols have the following significances: $R_2$ and $R_3$ together form a bridge of the part formula I*; $T_1=T_2=T_3=CH$; $T_4=N$; r=n=m=0; A=N; B=D=E=CH; $T=CR_4$; $R_4=O$—$CH_3$; W=H; $G=CH_2$; X=NH; Y=4-(tert-butyl)-phenyl; or a salt thereof.

Also very preferred is the compound with the designation 1-(4-isopropyl-3-methylanilino)-4-[2-(6-methyl-pyridin-3-yl)-ethyl]-isoquinoline, wherein, based on formula I, the symbols have the following significances: $R_2$ and $R_3$ together form a bridge of the part formula I*; $T_1=T_2=T_3=T_4=CH$; r=n=m=0; A=N; B=D=E=CH; $T=CR_4$; $R_4=CH_3$; W=H; $G=CH_2$—$CH_2$; X=NH; Y=4-isopropyl-3-methylphenyl; or a salt thereof.

A compound of the invention may be prepared by processes known per se for other compounds, especially whereby a) in order to prepare a compound of formula I, in which G is $C_1$–$C_2$-alkyleneoxy, $C_1$–$C_2$-alkylenethio, $C_1$–$C_2$-alkyleneimino, —O—, —S—, or —NH—, a compound of formula II:

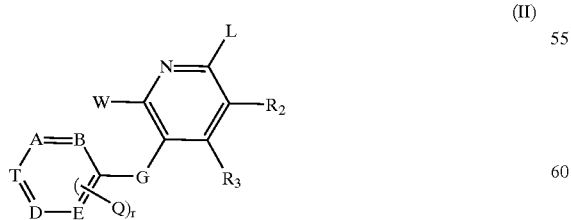

(II)

wherein r, A, B, D, E, T, W, Q, $R_2$ and $R_3$ have the significances given for a compound of formula I, G is $C_1$–$C_2$-alkyleneoxy, $C_1$–$C_2$-alkylenethio, $C_1$–$C_2$-alkyleneimino, —O—, —S—, or —NH— and L sig- nifies a nucleofugal leaving group, is reacted with a compound of formula III:

wherein n, $R_1$, $R_1'$, X and Y are as described for compounds of formula I;

b) in order to prepare a compound of formula I, in which G has the significance $C_2$–$C_6$-alkylene, $C_2$–$C_6$-alkenylene; or $C_2$–$C_6$-alkylene or $C_3$–$C_6$-alkenylene substituted by acyloxy or hydroxy; a compound of formula IV:

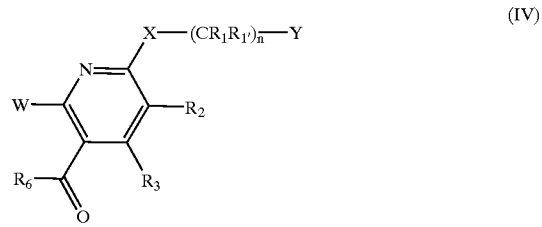

(IV)

wherein n, $R_1$, $R_1'$, X, Y, W, $R_2$ and $R_3$ are as described for a compound of formula I, and $R_6$ is H or $C_1$–$C_4$-alkyl, is reacted in the presence of a base with a compound of formula V:

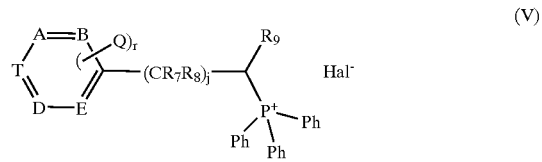

(V)

wherein r, A, B, D, E, T and Q are defined as for a compound of formula I, $R_7$, $R_8$ and $R_9$ independently of one another are H or $C_1$–$C_4$-alkyl, j is an integer between 0 and 4, Hal⁻ is a halide and Ph signifies phenyl, and the compound of formula I thus obtained, with $G=$—$CR_6=CR_9$—$(CR_7R_8)_j$— is converted, if desired, into another compound of formula I, for example by hydrogenation under catalysis with a secondary group metal or by addition of water and optional subsequent acylation;

c) in order to prepare a compound of formula I, wherein G is —$CH_2$—O—$CH_2$—, a compound of formula IV*:

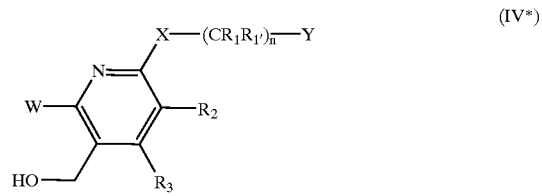

(IV*)

wherein n, $R_1$, $R_1'$, X, Y, W, $R_2$ and $R_3$ are as described for a compound of formula I, is reacted in the presence of a base with a compound of formula VI:

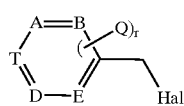
(VI)

wherein r, A, B, D, E, T and Q are defined as for a compound of formula I, and Hal is halogen;

d) in order to prepare a compound of formula I, wherein G is —CH$_2$—S—CH$_2$—, a compound of formula IV**:

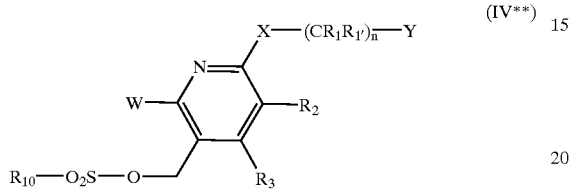
(IV**)

wherein n, R$_1$, R$_1'$, X, Y, W, R$_2$ and R$_3$ are as described for a compound of formula I, and R$_{10}$ is alkyl for example methyl, or alkylaryl for example tolyl, is reacted with a compound of formula VI*:

(VI*)

wherein r, A, B, D, E, T and Q are defined as for a compound of formula I, and M$^+$ is a singly charged metal cation, for example a sodium or a potassium cation;

e) in order to prepare a compound of formula I, wherein G is —CH$_2$—NH—CH$_2$—, a compound of formula IV***:

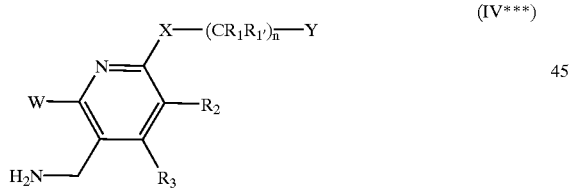
(IV***)

wherein n, R$_1$, R$_1'$, X, Y, W, R$_2$ and R$_3$ are as described for a compound of formula I, is reacted with a compound of formula VI**:

(VI**)

wherein r, A, B, D, E, T and Q are defined as for a compound of formula I, in the presence of hydrogen and a catalyst;

f) in order to prepare a compound of formula I, wherein G is methylene (—CH$_2$—), a compound of formula VII:

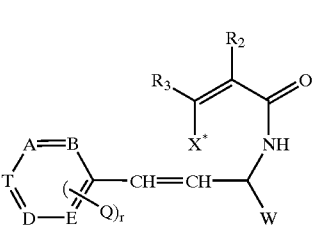
(VII)

wherein r, A, B, D, E, T, W, Q, R$_2$ and R$_3$ are defined as for a compound of formula I, X* is bromine, iodine or trifluoromethylsulfonyloxy, preferably iodine, and the double bond —CH=CH— is present in cis- or in trans-form, is reacted with palladium diacetate, and the compound of formula II* thus obtained, in which G is methylene, is reacted by introducing a nucleofugal group as described under "starting materials" to form a compound of formula II, in which G is methylene, whereby the further reaction to form a compound of formula I is carried out as described above under a);

whereby functional groups which are present in the starting compounds of processes a to f and are not intended to take part in the reaction, are present in protected form if necessary, and protecting groups that are present are cleaved, whereby the said starting compounds may also exist in the form of salts provided that a salt-forming group is present and a reaction in salt form is possible;

and, if so desired, a compound of formula I thus obtained or an N-oxide thereof is converted into another compound of formula I or an N-oxide thereof, a free compound of formula I or an N-oxide thereof is converted into a salt, an obtained salt of a compound of formula I or an N-oxide thereof is converted into the free compound or another salt, and/or a mixture of isomeric compounds of formula I or N-oxides thereof is separated into the individual isomers.

DETAILED DESCRIPTION OF THE PROCESS VARIANTS

In the more detailed description of the process below, r, n, A, B, D, E, T, G, Q, R$_1$, R$_1'$, R$_2$, R$_3$, W, X and Y are as defined for compounds of formula 1, unless otherwise indicated.

Regarding Process a):

In the compound of formula II, a nucleofugal leaving group L is especially halogen, above all bromine, iodine, or especially chlorine.

The reaction between the compound of formula II and the compound of formula III takes place in suitable, inert polar solvents, especially alcohols, e.g. lower alcohols, such as methanol, propanol or especially ethanol or n-butanol, or in a melt without the addition of a solvent, especially if one of the reaction partners is present in liquid form. The reaction takes place at elevated temperatures, preferably between about 60° C. and the reflux temperature of the solvent employed, for example under reflux conditions, or at a temperature between approximately 70 and approximately 110° C. The compound of formula III may also be used as a salt, for example as an acid addition salt with a strong acid, such as hydrogen halide, e.g. as a hydrochloride salt, or the corresponding acid, for example hydrochloric acid, may be added to an appropriate solvent, for example an ether such as dioxane.

Regarding Process b):

In formula V, the phenyl radicals found on the phosphorus may also be substituted as desired. The phenyl radicals found on the phosphorus are preferably unsubstituted. Instead of the said phosphorus compounds, the corresponding arsenic compounds may also be used. In formula V, Hal is iodide and especially chloride or bromide.

The base employed may be for example an alkali metal hydride such as sodium hydride, an alkali metal amide such as sodium amide, an alkyl lithium compound such as butyl lithium, an alkali metal alcoholate such as sodium ethanolate or sodium methanolate, an alkali metal carbonate such as sodium carbonate, or an alkaline earth metal carbonate such as magnesium carbonate.

The reaction is preferably carried out in the absence of water and oxygen in an appropriate solvent, for example dimethyl sulfoxide or tetrahydrofuran, at temperatures of between −10° C. and +80° C., preferably between 0° C. and 40° C., for example at room temperature.

The subsequent optional hydrogenation may be carried out under catalysis with a secondary group metal in a single solvent, for example water, alcohol, ethyl acetate, dioxane or tetrahydrofuran, in a mixture of these solvents or without solvents.

Elementary gaseous hydrogen is preferably used as a reagent of olefin. The reaction is carried out at normal pressure or in a hydrogen pressure of up to 200 atm and at temperatures of between 10° C. and 100° C.

The catalyst employed may be in particular platinum, palladium and nickel, as well as chemical comopounds containing these elements, for example palladium oxide or platinum oxide. The catalyst may be bound to a carrier, for example activated carbon, barium sulfate, strontium sulfate, calcium carbonate or aluminium oxide, or may be produced as a metallic sponge of a binary alloy by dissolving out one partner with acid or lye, as for example Raney nickel.

The optional subsequent addition of water may take place by reacting the olefin firstly with a mercury compound, for example mercury acetate, and then with sodium borohydride, or by reacting the olefin with water in the presence of an acid, for example sulphuric acid or nitric acid.

Regarding Process c):

The reaction is preferably effected in a solvent such as dimethyl sulfoxide or methylene chloride at temperatures of between 0° C. and boiling point of the solvent employed. The base used may be for example potassium hydroxide, a mixture of HgO and $HBF_4$, or silver carbonate or oxide. Alternatively, prior to the reaction with the halogen compound VI, the compound of formula IV* can also be converted into the corresponding alcoholate by deprotonation. In both cases, the reaction may be supported by adding phase transfer catalysts.

Regarding Process d):

The reaction is preferably effected in an appropriate polar solvent at temperatures of between 0° C. and boiling point of the solvent employed. The reaction can be supported by adding a phase transfer catalyst.

Alternatively, instead of the compound of formula VI*, the corresponding mercaptan may also be used. In this case, the reaction is preferably effected in known manner in a non-polar solvent such as benzene, preferably in the presence of DBU (1,8-diazabicyclo[5.4.0]undec-7-ene).

Regarding Process e):

The reaction is preferably effected in an inert solvent, for example an alcohol such as methanol, at temperatures of between 0° C. and 100° C., preferably between 50° C. and 90° C., in an autoclave with shaking or stirring motion, at a pressure of 50 to 150 atm hydrogen, especially at a pressure of 80 to 120 atm hydrogen. One of the secondary group metal catalysts described in process b) may be used as the catalyst. Raney nickel is most preferred.

Regarding Process f):

The reaction of formula VII is effected under metal catalysis, preferably with palladium diacetate, in the presence of tertiary amines such as trialkylamine, for example triethylamine, and/or in the presence of phosphines such as triarylphosphine, for example triphenylphosphine, preferably at a temperature of between 100° C. and 140° C., especially at a temperature of ca. 100° C. The solvent used may be for example N,N-dimethylformamide, acetonitrile or dimethyl sulfoxide, preferably N,N-dimethylformamide.

Additional Process Steps

In the additional process steps, carried out as desired, functional groups of the starting compounds which should not take part in the reaction may be present in unprotected form or may be protected for example by one or more protecting groups. The protecting groups are then wholly or partly removed according to one of the known methods. The end products of formula I may however also contain substituents, which also serve as protecting groups in starting compounds for the preparation of a compound of formula I. In the context of this text, a substituent of this type in a desired end product of formula I does not come under the designation "protecting group", although the context may infer this.

A compound of formula I can be converted to a corresponding N-oxide. The reaction is carried out with a suitable oxidizing agent, preferably a peroxide, for example m-chloroperbenzoic acid, in a suitable solvent, e.g. halogenated hydrocarbon, typically chloroform or dichloromethane, or in a lower alkanecarboxylic acid, typically acetic acid, preferably at a temperature between 0° C. and the boiling temperature of the reaction mixture, especially at about room temperature.

A compound of formula I (or an N-oxide thereof), wherein $R_2$ and $R_3$ together form a bridge of part formula I* and wherein Z is lower alkanoylamino, can be hydrolysed to a corresponding amino compound (Z=amino), for example by hydrolysis with an inorganic acid, especially hydrogen chloride (HCl) in an aqueous solution, further solvents possibly being added, preferably at elevated temperature, e.g. under reflux.

A compound of formula I (or an N-oxide thereof), wherein $R_2$ and $R_3$ together form a bridge of part formula I* and wherein Z is amino substituted by one or two radicals selected independently from lower alkyl, hydroxy-lower alkyl, and phenyl-lower alkyl, can be converted to a compound that is correspondingly substituted at the amino group, for example by reaction with a lower alkyl halide, if necessary a hydroxy-protected hydroxy-lower alkyl halide or phenyl-lower alkyl halide, under reaction conditions as described above. For the introduction of 2-hydroxy-lower alkyl substituents at the amino group Z, addition based on an epoxide (for example ethylene oxide) is also possible. The addition takes place especially in aqueous solution and/or in the presence of polar solvents, typically alcohols, for example methanol, ethanol, isopropanol, or ethylene glycol, ethers, typically dioxane, amides, typically dimethylformamide, or phenols, typically phenol, and also under non-aqueous conditions, in non-polar solvents, typically benzene and toluene, or in benzene/water emulsions, where applicable in the presence of acidic or basic catalysts, for example lyes, typically sodium hydroxide solution, or in the presence of solid-phase catalysts, typically aluminium oxide, that have been doped with hydrazine, in ethers, for example diethylether, generally at temperatures from about 0° C. to the boiling temperature of the corresponding reaction mixture, preferably between 20° C. and reflux temperature, if necessary under increased pressure, e.g. in a sealed tube, whereby the boiling temperature may also be exceeded, and/or under inert gas, typically nitrogen or argon. Reductive alkylation of an amino group Z with a lower alkanal, a phenyl lower alkanal, or a hydroxy-lower alkanal, if necessary hydroxy-protected, is also possible. Reductive alkylation takes place preferably under hydrogenation in the presence of a catalyst, especially a noble metal catalyst, typically platinum or especially palladium, which is preferably bound to a carrier, such as carbon, or in the presence of a heavy-metal catalyst, typically Raney-Nickel, at normal pressure or at pressures from 0.1 to 10 megapascal (MPa), or under reduction using complex hydrides, typically boranes, especially alkali cyanoborohydride, for example sodium cyanoborohydride, in the presence of a suitable acid, preferably a relatively weak acid, typically a lower alkanecarboxylic acid or especially a sulfonic acid, such as p-toluenesulfonic acid; in customary solvents, for example alcohols, such as methanol or ethanol, or ethers, for example cyclic ethers, such as tetrahydrofuran, in the presence or absence of water.

In a compound of formula I (or an N-oxide thereof), wherein $R_2$ and $R_3$ together form a bridge of part formula I*, an amino group Z can be converted by acylation to an amino group substituted by lower alkanoyl, benzoyl, substituted benzoyl, or phenyl-lower alkoxycarbonyl, wherein the phenyl radical is unsubstituted or substituted. The corresponding acids comprise a free carboxy group or are present as reactive acid derivatives thereof, for example derivative activated esters or reactive anhydrides, and also reactive cyclic amides. The reactive acid derivatives may also be formed in situ.

A nitro group Z in a compound of formula I, wherein $R_2$ and $R_3$ together form a bridge of part formula I*, can be reduced to an amino group, for example by reduction with metals or by selective hydrogenation; for example by a reaction with magnesium/ammonium sulfate in a water/alcohol mixture, such as methanol/water, at an elevated temperature, e.g. between 30 and 60° C. [see Synth. Commun. 25(2), 4025–8 (1995)]; by a reaction with zinc/borohydride in an acid amide such as dimethylformamide, at temperatures below room temperature, e.g. at ca. 0° C.; by a reaction with 1,1'-dioctyl-4,4'-bipyridinium dibromide/sodium tetrathionate/potassium carbonate in water/halogenated hydrocarbon mixtures, e.g. water/methylene chloride mixtures, at an elevated temperature, e.g. 25 to 35° C. [see Tetrahedron Lett. 34(46), 7445–6 (1993)]; with sodium borohydride on Amberlyte IRA-400 ion exchanger in the chloride form In an alcohol such as methanol/water, at preferred temperatures of between 0 and 40° C. [see Synthetic Commun. 19(5/6), 805–11 (1989)]; with potassium borohydride in a halogenated hydrocarbon/alcohol mixture, e.g. dichloromethane/methanol, at preferred temperatures of between 10 and 35° C. [see Synthetic Commun. 19(17), 3047–50 (1989)]; with sodium borohydride in dioxane; with borane in tetrahydrofuran; by hydrogenation in the presence of Pd/C in an alcohol at a preferred temperature of 0 to 35° C. and in the presence of ammonium formate [see Tetrahedron Lett. 25(32), 3415–8 (1989)]; with titanium tetrachloride/lithium aluminium hydride or titanium tetrachloride/magnesium in an ether such as tetrahydrofuran [see Bull. Chem. Soc. Belg. 97(1), 51–3 (1988]; or with ferric ammonium chloride/water at an elevated temperature, preferably under reflux [Synth. Commun. 22, 3189–95 (1992)].

In a compound of formula I, wherein G is $C_1$–$C_6$-alkylene substituted by acyloxy and the other radicals are as defined under formula I, the acyl radical can be removed by hydrolysis, resulting in the corresponding compound of formula I, in which G is $C_1$–$C_6$-alkylene substituted by hydroxy. The hydrolysis is carried out preferably under the usual conditions, typically in the presence of acids or bases, such as HCl or NaOH, in aqueous solution or a suitable solvent or solvent mixture.

From a compound of formula I wherein G is $C_2$–$C_6$-alkylene substituted by hydroxy, a compound of formula I wherein G is $C_2$–$C_6$-alkylene can also be prepared by dehydration. From a compound of formula I wherein G is $C_2$–$C_6$-alkenylene, a compound of formula I wherein G is $C_2$–$C_6$-alkylene can also be prepared by hydrogenation. The reaction in this case is preferably effected with catalytic hydrogenation under the above-mentioned conditions.

A compound of formula I, in which G is hydroxymethylene, may be prepared for example by oxidation of a compound of formula I in which G is methylene, for example by heating such as boiling over activated carbon in an alcohol, for example methanol, in the presence of air or an oxygen-enriched atmosphere. In part of this reaction, the corresponding ketone is also formed (G=—CO—), which can then be reduced for example with complex metal hydrides such as $LiAlH_4$ or $NaBH_4$ to form the secondary alcohol (G=hydroxymethylene).

A compound of formula I, in which G is methylene substituted by acyloxy, may be obtained for example by esterification of a corresponding carboxylic acid with a compound of formula I, in which G is hydroxymethylene. Esterification is carried out according to known methods.

A compound of formula I, in which $R_4$ is etherified hydroxy, may be converted by hydrolysis into a compound of formula I, in which $R_4$ is hydroxy, for example by heating in the presence of trimethylsilyl iodide and an appropriate solvent, for example chloroform.

A compound of formula I, in which $R_4$ is esterified hydroxy, may be obtained for example by esterification of a corresponding carboxylic acid with a compound of formula I, in which $R_4$ is hydroxy, under known reaction conditions.

A compound of formula I, in which $R_4$ is halogen, may be obtained for example by reacting a compound of formula I, in which $R_4$ is hydroxy, with an inorganic acid halide, for example phosphoryl chloride ($POCl_3$), phosgene ($COCl_2$) or thionyl chloride ($SOCl_2$) to introduce $R_4$=Cl, or another appropriate reagent.

A compound of formula I, in which $R_4$ is halogen, may be transformed by nucleophilic substitution—using the corresponding nucleophiles and employing appropriate known reaction conditions—into compounds of formula I, in which $R_4$ is unsubstituted, mono- or di-substituted amino, mercapto or lower alkylthio.

General Process Conditions

All process steps described here can be carried out under known reaction conditions, preferably under those specifically mentioned, in the absence of or usually in the presence of solvents or diluents, preferably those that are inert to the reagents used and able to dissolve them, in the absence or presence of catalysts, condensing agents or neutralisiing agents, for example ion exchangers, typically cation exchangers, for example in the $H^+$ form, depending on the type of reaction and/or reactants at reduced, normal, or elevated temperature, for example in the range from –100° C. to about 190° C., preferably from about –80° C. to about 150° C., for example at –80to –60° C., at room temperature, at –20 to 40° C. or at the boiling point of the solvent used, under atmospheric pressure or in a closed vessel, if need be under pressure, and/or in an inert, for example an argon or nitrogen, atmosphere.

The invention relates also to those embodiments of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention under those process conditions, and further processes the said compound in situ. In the preferred embodiment, one starts from those starting materials which lead to the compounds described hereinabove as preferred, particularly as especially preferred, particularly preferred, primarily preferred and/or preferred above all.

In the preferred embodiment, a compound of formula I (or N-oxides thereof) is prepared according to the processes and process steps defined in the Examples.

The compounds of formula I (or N-oxides thereof), including their salts, are also obtainable in the form of hydrates, or their crystals can include for example the solvent used for crystallisation (present as solvates).

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

The starting materials of formulae II to VII are known, capable of being prepared according to known processes, or commercially obtainable; in particular, they can be prepared using processes as described in the Examples.

In the preparation of starting materials, existing functional groups which do not participate in the reaction should, if necessary, be protected. Preferred protecting groups, their introduction and their removal are described above or in the examples. In place of the respective starting materials and transients, salts thereof may also be used for the reaction, provided that salt-forming groups are present and the reaction with a salt is also possible.

Where the term starting materials is used hereinbefore and hereinafter, the salts thereof are always included, insofar as reasonable and possible.

Compounds of formula II, in which G is $C_1$–$C_2$-alkyleneoxy, $C_1$–$C_2$-alkylenethio, $C_1$–$C_2$-alkyleneimino, oxa, thia or imino and the remaining symbols are defined as for formula I, may be prepared for example by reacting a compound of formula VIII,

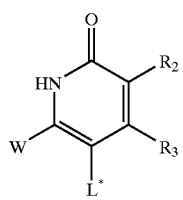

(VIII)

wherein L* signifies a nucleofugal leaving group, especially halogen, for example bromine, and $R_2$, $R_3$ and W are defined as for a compound of formula I, with a compound of formula VI***:

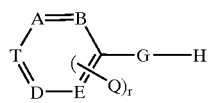

(VI***)

wherein G is $C_1$–$C_2$-alkyleneoxy, $C_1$–$C_2$-alkylenethio, $C_1$–$C_2$-alkyleneimino, or also oxa, thia or imino, and A, B, D, E, T, Q and r are defined as for compounds of formula I, preferably under conditions analogous to those mentioned in process a) for the reaction of a compound of formula II with a compound of formula III. A compound of formula II* is thus obtained:

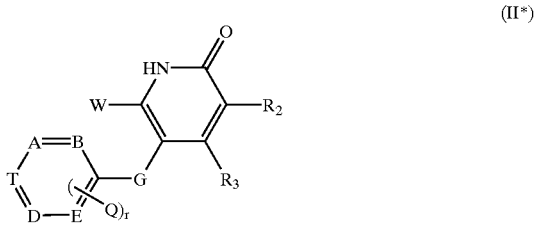

(II*)

wherein $R_2$ and $R_3$, as well as A, B, D, E, T, Q, W and r, are defined as for a compound of formula I, and wherein G is $C_1$–$C_2$-alkyleneoxy, $C_1$–$C_2$-alkylenethio, $C_1$–$C_2$-alkyleneimino, or also oxa, thia or imino.

From this, the corresponding compound of formula II can be produced by introducing a nucleofugal group L*, as defined for L under formula II, using an inorganic acid chloride, for example phosphoryl chloride ($POCl_3$), phosgene ($COCl_2$) or thionyl chloride ($SOCl_2$) to introduce L*=Cl, or using another reagent which is suitable for the reaction of a compound of formula II* into one of formula II.

A compound of formula V may be obtained by reacting triarylphosphine, for example triphenylphosphine, with a compound of formula IX:

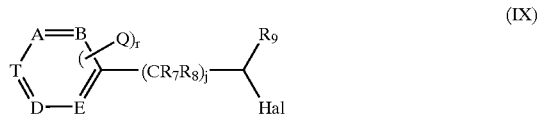

(IX)

wherein A, B, D, E, T, Q, r, $R_7$, $R_8$, $R_9$, j and Hal are defined as for a compound of formula V, in an inert solvent, for example toluene, at temperatures of between 20° C. and 110° C., especially between 60° C. and 80° C.

A compound of formula IV is obtainable for example by the following reaction sequence. A compound of formula X:

(X)

wherein $R_2$, $R_3$ and W are defined as for a compound of formula I, is reacted first of all with an inorganic acid chloride, for example phosphoryl chloride, ($POCl_3$), phosgene ($COCl_2$) or thionyl chloride ($SOCl_2$), in an appropriate solvent, such as acetonitrile or dioxane, or in a mixture of such solvents, at temperatures of between 20° C. and 80° C., for example 50° C., to form a compound of formula XI:

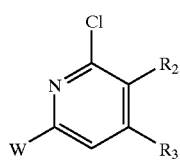
(XI)

This compound of formula XI is subsequently reacted with a compound of formula III, preferably under reaction conditions that are similar to those mentioned for process a) during the reaction of a compound of formula II with a compound of formula III. A compound of formula XII is thus obtained:

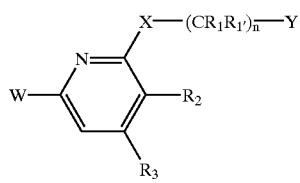
(XII)

and is reacted with a 2,4,6-tri-($C_1$–$C_4$-alkyl)-1,3,5-trioxane or 1,3,5-trioxane and an alkyl hydroperoxide, for example tert-butylhydroperoxide, in the presence of an iron(II) compound, for example iron(II) sulfate, at temperatures of between 60° C. and 100° C., for example 80° C., in an appropriate solvent, for example acetonitrile and trifluoroacetic acid, to form a compound of formula XIII:

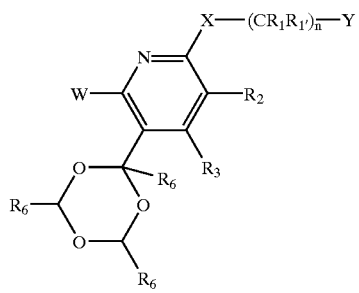
(XIII)

wherein $R_2$ and $R_3$ as well as X, Y, n, W, $R_1$ and $R_{1'}$ are defined as for a compound of formula I, and wherein $R_6$ is H or $C_1$–$C_4$-alkyl. The reaction of a compound of formula XIII in an aqueous acid, for example 10% aqueous sulfuric acid, at temperatures of between 75° C. and 110° C., preferably 90 to 100° C., yields a compound of formula IV.

The preparation of the compounds of formula I, in which G is —$CH_2$—O—$CH_2$—, $CH_2$—S—$CH_2$— or —$CH_2$—NH—$CH_2$—, may take place for example starting with a compound of formula IV, in which n, $R_1$, $R_{1'}$, X, Y, W, $R_2$ and $R_3$ are defined as for a compound of formula I.

By reacting a compound of formula IV in known manner with a reduction agent, for example lithium aluminium hydride, in an appropriate solvent, such as diethylether or tetrahydrofuran, a compound of formula IV* for process c) is obtained, to prepare the compounds of formula I in which G is —$CH_2$—O—$CH_2$—.

A compound of formula IV* may be transformed into a compound of formula IV by a reaction with an alkylsulfonyl chloride, for example methanesulfonic acid chloride or an alkylarylsulfonyl chloride, for example toluenesulfonic acid chloride, and this compound of formula IV is used in accordance with process d) to prepare the compounds of formula I, in which G is —$CH_2$—S—$CH_2$—.

The reaction of a compound of formula IV with ammonia makes a compound of formula XIV obtainable in known manner:

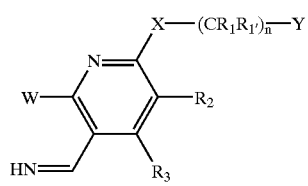
(XIV)

wherein n, $R_1$, $R_{1'}$, X, Y, W, $R_2$ and $R_3$ are defined as for a compound of formula I. By reacting this compound with a reduction agent, for example lithium aluminium hydride, under the above-mentioned conditions, or with sodium borohydride, a compound of formula IV*** is obtained for process e) in order to prepare the compounds of formula I in which G is —$CH_2$—N—$CH_2$—.

A compound of formula VII in which G is methylene is obtainable for example by the following reaction sequence. A compound of formula VI is reacted first of all with triaryl phosphine, for example triphenyl phosphine, analogously to the above-mentioned reaction of compounds of formula IX with triaryl phosphine, to form a compound of formula V*:

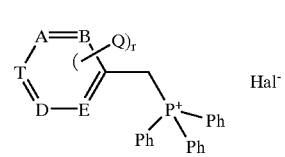
(V*)

wherein r, A, B, D, E, T and Q are defined as for a compound of formula I, and Hal is halide and Ph is phenyl. A compound of formula V* is subsequently reacted with a compound of formula XV:

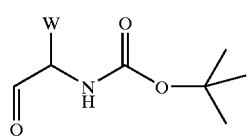
(XV)

wherein W is defined as for a compound of formula I, in the presence of a base, for example under conditions such as those described in process b), thus producing an (E/Z) mixture of a compound of formula XVI:

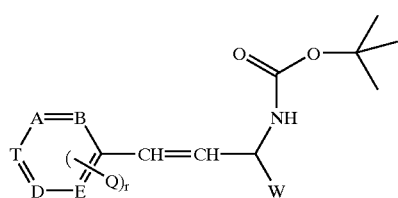
(XVI)

By cleaving the tert.-butyl carbamate (BOC) group of a compound of formula (XVI) under conventional conditions, for example under the conditions described in Th. W. Greene and P. G. M. Wuts, "Protective Groups in Organic Synthesis", Wiley, N.Y. 1991 (2nd ed., pp 328–330), the primary amine is obtained, which is then reacted with a compound of formula XVII:

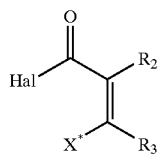

(XVII)

wherein X* is defined as for a compound of formula VII and Hal is halogen, especially chlorine, thus producing an (E/Z) mixture of a compound of formula VII. The reaction is effected for example in acetonitrile as the solvent and in the presence of 4-methyl-morpholine.

The remaining starting materials are known, capable of being prepared according to known processes, or commercially available; or in particular, they can be prepared using processes as described in the examples.

Pharmaceutical Preparations, Methods, and Uses

The present invention relates also to pharmaceutical compositions that comprise a compound of formula I (or an N-oxide thereof) as active ingredient and that can be used especially in the treatment of the diseases mentioned at the beginning. Preparations for enteral administration, such as nasal, buccal, rectal or, especially, oral administration, and for parenteral administration, such as intravenous, intramuscular or subcutaneous administration, to warm-blooded animals, especially humans, are especially preferred. The preparations contain the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The invention relates also to pharmaceutical preparations for use in a method for the prophylactic or especially therapeutic treatment of the human or animal body, to a process for the preparation thereof (especially in the form of compositions for the treatment of tumours) and to a method of treating the above-mentioned diseases, primarily tumour diseases, especially those mentioned above.

The invention relates also to processes and to the use of compounds of formula I (or an N-oxide thereof) for the preparation of pharmaceutical preparations which comprise compounds of formula I (or an N-oxide thereof) as active component (active ingredient).

If desired, the said pharmaceutical compositions may also contain further active components, for example cytostatics, and/or may be used in combination with known therapeutic processes, for example the administration of hormones or radiation.

Preference is for a pharmaceutical preparation which is suitable for administration to a warm-blooded animal, especially humans or commercially useful mammals suffering from a disease which responds to an inhibition of angiogenesis or of VEGF-receptor tyrosine kinase, for example psoriasis or especially a neoplastic disease, comprising an effective quantity of a compound of formula I (or an N-oxide thereof) for the inhibition of angiogenesis or of VEGF-receptor tyrosine kinase, or a pharmaceutically acceptable salt thereof, if salt-forming groups are present, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against said diseases a new compound of formula I (or an N-oxide thereof) or a pharmaceutically acceptable salt thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories or capsules. Examples are capsules containing from about 0.05 g to about 1.0 g of active substance.

The pharmaceutical preparations of the present invention are prepared in a manner known per se, for example by means of conventional mixing, granulating, coating, dissolving or lyophilising processes.

The invention relates likewise to a process or a method for the treatment of one of the pathological conditions mentioned hereinabove, especially a disease which responds to an inhibition of the VEGF-receptor tyrosine kinase or an inhibition of angiogenesis, especially a corresponding neoplastic disease or also psoriasis. The compounds of formula I (or an N-oxide thereof) can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions. In the case of an individual having a bodyweight of about 70 kg the daily dose administered is from approximately 0.1 g to approximately 5 g, preferably from approximately 0.5 g to approximately 2 g, of a compound of the present invention.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of VEGF-receptor tyrosine kinase or an inhibition of angiogenesis, especially a neoplastic disease or also psoriasis, in particular if the said disease responds to an inhibition of VEGF-receptor tyrosine kinase or angiogenesis.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, for the preparation of a pharmaceutical formulation for the therapeutic and also prophylactic management of one or more of the diseases mentioned hereinabove, especially a neoplastic disease or also psoriasis, in particular if the disease responds to an inhibition of VEGF-receptor tyrosine kinase or angiogenesis.

EXAMPLES

The following Examples serve to illustrate the invention without limiting its scope.

Temperatures are measured in degrees Celsius. Unless otherwise indicated, the reactions take place at room temperature.

The $R_f$ values which indicate the ratio of the distance moved by each substance to the distance moved by the eluant front are determined on silica gel thin-layer plates (Merck, Darmstadt, Germany) by thin-layer chromatography using the respective named solvent systems.

HPLC Gradient:

$$\text{gradient}_{20-100}\ 20\% \rightarrow 100\%\ a)\ \text{in b) for 13 min}+5\ \text{min 100\% a)}.$$

Eluent a): Acetonitrile+0.05% TFA; eluant b): water+0.05% TFA. Column (250×4.6 mm) packed with reversed-phase material C18-Nucleosil (5 μm mean particle size, with silica gel covalently derivatised with octadecylsilanes, Macherey & Nagel, Duren, Germany). Detection by UV absorption at 215 nm. The retention times ($t_{Ret}$) are given in minutes. Flow rate: 1 ml/min.

The short forms and abbreviations used have the following definitions:

| | |
|---|---|
| abs. | absolute |
| brine | saturated sodium chloride solution |
| dil. | diluted |
| DIPE | diisopropyl ether |
| DMF | N,N-dimethylformamide |
| DMSO | dimethyl sulfoxide |
| EtOAc | ethyl acetate |
| Ex. | Example |
| FAB-MS | fast atom bombardment mass spectroscopy |
| h | hour(s) |
| i.a. | inter alia |
| min | minute(s) |
| m.p. | melting point |
| rac. | racemic |
| RT | room temperature |
| RE | rotary evaporator |
| sat. | saturated |
| TFA | trifluoroacetic acid |
| THF | tetrahydrofuran (dist. over Na/benzophenone) |
| TLC | thin-layer chromatograph |

Example 1

Under an $N_2$ atmosphere, 250 mg (0.93 mmol) of 1-chloro-4-(2-pyridin-3-yl-ethyl)-isoquinoline in 2.9 ml of abs. ethanol are mixed with 131 mg (1.02 mmol) of 4-chloro-aniline and 0.23 ml of 4 N HCl/dioxane, and stirred for 8 h at 80° C. The mixture is cooled to RT, filtered and the residue washed with acetonitrile. The residue is dissolved in 4 ml of water, then 0.9 ml of sat. $NH_3$ solution are added, stirring is effected for 10 min, the precipitate is filtered off and washed with water. Recrystallisation from acetonitrile yields 1-(4-chloroanilino)-4-[2-(pyridin-3-yl)-ethyl]-isoquinoline; m.p.157–158° C.

The starting material is prepared as follows:

Step 1.1: 470 ml (4.28 mol) of N-methylmorpholine, followed by 224 ml (2.98 mol) of allylamine are added under ice cooling to 750 g (2.81 mol) of 2-iodo-benzoic acid chloride in 7.5 l of acetonitrile, and stirred for 60 min at RT. The precipitate is filtered off and the filtrate concentrated by evaporation on a RE. The residue of evaporation is dissolved in 4 l of EtOAc and 4 l of water, the water phase is separated and extracted twice with EtOAc. The organic phases are washed with water, 0.1 N HCl, water, sat. $Na_2CO_3$, water and brine, dried ($Na_2SO_4$) and concentrated by evaporation. Stirring of the residue in 2.5 l of hexane and filtering yields 2-iodo-benzoic acid allylamide; m.p. 105–106° C.

Step 1.2: Under an $N_2$ atmosphere, 985 ml (7.07 mol) of triethylamine, 892 g (3.21 mol) of tetra-$^n$butylammonium chloride and 12.77 g (57 mmol) of $Pd(OAc)_2$ are added to 815 g (2.8 mol) of 2-iodo-benzoic acid allylamide in 4.5 l of DMF, and heated to 100° C. After 4 h, cooling is effected to RT, and the mixture is partially concentrated by evaporation on a RE. The residue is partitioned between 5 l of water and 5 l of EtOAc, the water phase is separated and extracted twice with EtOAc. The organic phases are washed with water, 0.1 N HCl, water and brine, dried ($Na_2SO_4$) and concentrated by evaporation. Column chromatography ($SiO_2$, EtOAc/toluene 1:1) and crystallisation from toluene yields 4-methyl-2H-isoquinolin-1-one; m.p. 175–176° C.

Step 1.3: In an apparatus equipped with a mechanical stirrer ($N_2$ gas), 135 g (848 mmol) of 4-methyl-2H-isoquinolin-1-one in 2.0 l of DMSO are heated to 50° C. After removing the oil bath, 108 g (447 mmol) of $Cu(NO_3)_2$.$3H_2O$ are added. Then, whilst cooling, 432 g (1.81 mol) of $Na_2S_2O_8$ are added in portions, and finally 162 g (1.91 mol) of $NaNO_3$. After stirring for 2 h at 50° C., the mixture is cooled to 10° C., mixed with 4 l of water and stirred for 10 min. 1-oxo-1,2-dihydro-isoquinoline-4-carbaldehyde can be filtered from the light green suspension and washed with water; m.p. 222–223° C. The filtrate is extracted 3 more times with EtOAc. The EtOAc phases are washed with water (3×) and brine, dried ($Na_2SO_4$) and concentrated by evaporation. Column chromatography of the residue ($SiO_2$, methylene chloride/toluene/acetone 2:2:1) yields further 1-oxo-1,2-dihydro-isoquinoline-4-carbaldehyde.

Step 1.4: Under an $N_2$ atmosphere,147 g (377 mmol) of triphenyl-(pyridin-3-yl-methyl)-phosphonium chloride in 2.2 l of THF are mixed with 44.1 g (393 mmol) of potassium-tert-butylate and stirred for 30 min. The suspension is heated to 50° C. and a mixture of 50.0 g (289 mmol) of 1-oxo-1,2-dihydro-isoquinoline-4-carbaldehyde and 2.2 l of THF is added dropwise and finally stirred for 10 h at 60° C. To the cooled reaction mixture is added 700 ml of water and then the THF is evaporated off on a RE. The residue is taken up in 5 l of water and 8 l of EtOAc, the water phase is separated and extracted 3 more times with EtOAc. The organic phases are washed with water and with brine, combined, dried ($Na_2SO_4$) and left to stand over night. A solid separates from the mixture and is filtered off and washed with EtOAc [→(E) 4-[2-(pyridin-3-yl)-vinyl]-2H-isoquinolin-1-one]. The filtrate is extracted twice with 1 N HCl and then discarded. The acidic aqueous phases are immediately rendered basic with sat. $Na_2CO_3$ solution and extracted 3 times with EtOAc. The organic phases are washed with water and brine, dried ($Na_2SO_4$) and concentrated by evaporation. Column chromatography ($SiO_2$, EtOAc/ethanol 19:1→9:1) yields first of all (Z) 4-[2-(pyridin-3-yl)-vinyl]-2H-isoquinolin-1-one, followed by an (E/Z) mixture of 4-[2-(pyridin-3-yl)-vinyl]-2H-isoquinolin-1-one. (E) 4-[2-(pyridin-3-yl)-vinyl]-2H-isoquinolin-1-one: m.p. 222–224° C.; $^1$H NMR (DMSO-$d_6$) δ11.57 (sb, HN), 8.80 (s, 1H), 8.44 (d, 1H), 8.26 (d, 1H), 8.12 (m, 2H, m), 7.79 (t, 1H), 7.68 (d, J=16.3 Hz, 1H), 7.56 (m, 2H), 7.39 (dd, 1H), 7.07 (d, J=16.3 Hz 1H). (Z) 4-[2-(pyridin-3-yl)-vinyl]-2H-isoquinolin-1-one: $^1$H NMR (DMSO-$d_6$) δ11.24 (sb, HN), 8.39 (s, 1H), 8.32 (d, 1H), 8.25 (d, 1H), 7.71 (t, 1H), 7.65 (d, 1H), 7.54 (m, 2H), 7.21 (dd, 1H), 6.90 (s, 1H), 6.81 (s, 2H$^{Olef.}$).

Step 1.4.1: 120 g (732 mmol) of 3-chloromethylpyridine hydrochloride are added in portions to an ice-cooled 2-phase mixture of 116.4 g (1.099 mol) of Na$_2$CO$_3$ in 1130 ml of water and 550 ml of toluene. The mixture is stirred at 0° C. until a clear solution is obtained, the aqueous phase is separated and extracted 3 times with 0.4 l of toluene. The toluene phases are dried (Na$_2$SO$_4$) and concentrated by evaporation on a RE (10 mbar, 30° C.) until attaining a volume of 0.5 l. 383.7 g (1.46 mol) of triphenylphosphine are added to the yellowish solution and stirring effected under a N$_2$ atmosphere for several days at 80° C. Triphenyl-(pyridin-3-yl-methyl)-phosphonium chloride separates and can be filtered off and washed with toluene and hexane; $^1$H-NMR (DMSO-d$_6$) δ8.47 (m, 1H$^{Py}$), 8.18 (sb, 1H$^{Py}$), 7.91 (m, 3H), 7.72 (m, 12H), 7.37 (m, 1H$^{Py}$), 7.26 (m, 1H$^{Py}$), 5.33 (d, J=15 Hz, H$_2$C).

Step 1.5: 80 g (322 mmol) of an (E/Z) mixture of 4-[2-(pyridin-3-yl)-vinyl-2H-isoquinolin-1-one in 3100 ml of methanol/THF 1:1 are hydrogenated in the presence of 15.2 g of Pd/C (10%). Filtration and concentration by evaporation yield the crude product. Recrystallisation by dissolving in 650 ml of boiling ethanol, hot filtration, cooling and addition of 1 l of diethylether and 0.2 l of hexane yield colourless 4-[2-(pyridin-3-yl)-ethyl]-2H-isochinolin-1-one; m.p.187–188° C.

Step 1.6: 3.12 g (12.48 mmol) of 4-[2-(pyridin-3-yl)-ethyl]-2H-isoquinolin-1-one in 82 ml of acetonitrile are mixed, whilst excluding air, with 2.86 ml (31.2 mmol) of phosphorus oxychloride and 6.2 ml of 4 N HCl in dioxane and stirred for 19 h at 60° C. After cooling to RT, 177 ml of water and sat. Na$_2$CO$_3$ solution are added and extracted 3 times with EtOAc. The organic phases are washed with water and brine, dried, (Na$_2$SO$_4$) and concentrated by evaporation to 1-chloro-4-[2-(pyridin-3-yl)-ethyl]-isoquinoline; m.p. 133–135° C.

Example 2

240 mg (0.90 mmol) of (Z) 1-chloro-4-(2-pyridin-3-yl-vinyl)-isoquinoline in 2.8 ml of abs. ethanol are mixed, whilst excluding air, with 167 mg (0.90 mmol) of 3-bromo-4-methylaniline and 0.23 ml of 4 N HCl/dioxane, and stirred for 6 h at 80° C. The mixture is cooled to RT, 4 ml of water and 0.87 ml of sat. ammonia solution are added, and stirring effected for 10 min. The suspension is dissolved in EtOAc and water, the water phase separated and extraction effected twice more with EtOAc. The EtOAc phases are washed with water and brine, dried (Na$_2$SO$_4$) and concentrated by evaporation to a residual volume of ≈1 ml. The addition of DIPE leads to crystallisation of (Z) 1-(3-bromo-4-methylanilino)-4-[2-(pyridin-3-yl)-vinyl]-isoquinoline; m.p.170–171° C.

The starting material is prepared as follows:

Step 2.1: Under a N$_2$ atmosphere, 248 mg (1.00 mmol) of (Z) 4-[2-(pyridin-3-yl)-vinyl]-2H-isoquinolin-1-one (step 1.4) in 4 ml of acetonitrile are mixed with 230 μl (2.5 mmol) of phosphorus oxychloride and 0.5 ml of 4 N HCl in dioxane and stirred for 4 h at 60° C. After cooling to RT, 22 ml of water and saturated Na$_2$CO$_3$ solution are added, the water phase is separated and extracted 3 times with EtOAc. The organic phases are washed with water and brine, dried (Na$_2$SO$_4$) and concentrated by evaporation to (Z) 1-chloro-4-[2-(pyridin-3-yl)-vinyl]-isoquinoline; $^1$H NMR (DMSO-d$_6$) δ8.35 (m, 2H), 8.27 (s,1H), 8.06 (m, 2H), 7.9 (m, 2H), 7.37 (d, 1H), 7.18 (m, 2H), 7.08 (d, J=10 Hz, 1H$^{Olef.}$).

Example 3

150 mg (0.56 mmol) of (E) 1-chloro-4-(2-pyridin-3-yl-vinyl)-isoquinoline in 1.8 ml of abs. ethanol are reacted, analogously to example 2, with 105 mg (0.56 mmol) of 3-bromo-4-methylaniline and 0.14 ml of 4 N HCl/dioxane. Column chromatography (SiO$_2$, EtOAc/toluene 1:3) yields (E) 1-(3-bromo-4-methylanilino)-4-[2-(pyridin-3-yl)-vinyl]-isoquinoline; m.p.196–197° C.

The starting material is prepared as follows:

Step 3.1: 400 mg (1.61 mmol) of (E) 4-[2-(pyridin-3-yl)-vinyl]-2H-isoquinolin-1-one (step 1.4) in 7 ml of acetonitrile are reacted, analogously to step 2.1, with 368 μl (4.0 mmol) of phosphorus oxychloride and 0.8 ml 4 N HCl in dioxane to (E) 1-chloro-4-[2-(pyridin-3-yl)-vinyl]-isoquinoline; m.p. 151–152° C.

The following compounds of formula Ia are obtained analogously to example 1 by reacting 1-chloro-4-(2-pyridin-3-yl-ethyl)-isoquinoline with a compound of formula Y—NH$_2$, in which Y is defined as for formula I:

(Ia)

| Ex. | Y—NH | m.p. [° C.] |
|---|---|---|
| 4 | 3-bromo-4-methylphenyl-NH | 138 |
| 5 | 4-tert-butylphenyl-NH | 81 |
| 6 | 3-(trifluoromethyl)phenyl-NH | 150 |
| 7* | 3-chloro-5-(trifluoromethyl)phenyl-NH | 156 |

-continued

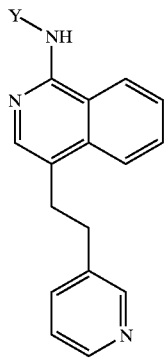

(Ia)

| Ex. | Y—NH | m.p. [° C.] |
|---|---|---|
| 8 | (4-isopropyl-3-methylphenyl)NH | 133–134 |
| 9* | (3-bromo-4-ethylphenyl)NH | 119 |
| 10 | (3-tert-butylphenyl)NH | 133–134 |
| 11 | (3,4-bis(trifluoromethyl)phenyl)NH | 124–125 |
| 12 | (3,5-bis(trifluoromethyl)phenyl)NH | 174 |
| 13 | (4-chloro-3-trifluoromethylphenyl)NH | 159 |

-continued

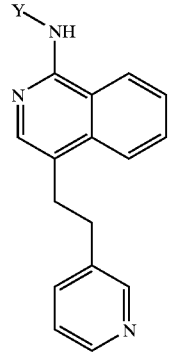

(Ia)

| Ex. | Y—NH | m.p. [° C.] |
|---|---|---|
| 14 | (3-bromo-5-trifluoromethylphenyl)NH | |
| 15 | (phenyl)NH | |

*The starting materials of formula Y—NH$_2$ in examples 7 and 9 are prepared as follows: Example 7 (preparation of 5-amino-3-chlorobenzotrifluoride: (see also: EP 0516 297 A$_1$)

Step 1: 56.7 ml of 96% sulphuric acid are added dropwise over 30 min to a brown solution of 90 g (374 mmol) of 4-amino-3-chloro-5-nitro-benzotrifluoride (Maybridge; Tintagel/England) in 500 ml of ethanol (exothermic). After heating to 75° C., 64.53 g (935 mmol) of sodium nitrite are added in portions over 1 h (gas evolution). Stirring is effected for 2.5 h at 75° C., followed by cooling to RT. The reaction mixture is poured onto 1.5 l of ice water and extracted 4 times with diethylether. Washing of the organic phase with 0.1 N HCl, sat. NaHCO$_3$ solution and brine, drying (Na$_2$SO$_4$) and concentrating by evaporation yield a brown oil. Column chromatography (SiO$_2$; hexane) yields 5-chloro-3-trifluoromethyl-nitrobenzene as an oil; $^1$H-NMR (DMSO-d$_6$) δ8.62 (m, 1 H), 8.46 (m, 2H).

Step 2: 92 g (0.408 mol) of 5-chloro-3-trifluoromethyl-nitrobenzene in 1 l of methanol are hydrogenated in the presence of 10.17 g of Raney nickel. The reaction mixture is filtered through Celite/activated carbon and the residue washed with methanol. Concentration of the filtrate by evaporation yields the oily 5-amino-3-chloro-benzotrifluoride; $^1$H-NMR (DMSO-d$_6$) δ6.80 (m, 3H), 5.92 (s, H$_2$N).

Example 9

(Preparation of 3-bromo-4-ethylaniline)

Hydrogenation of 4.45 g (19 mmol) of 3-bromo-4-ethyl-nitrobenzene (for preparation see *Macromolecules* 1995, 28, 5618) in 100 ml of ethanol in the presence of 1 g of Raney nickel, followed by filtration, concentration by evaporation and chromatography (SiO$_2$; methylenechloride), yields 3-bromo-4-ethyl-aniline; $^1$H NMR (CDCl$_3$) δ6.94 (d, 1H), 6.82 (s, 1H), 6.50 (d, 1H), 3.50 (s, H$_2$N), 2.57 (q, 2H), 1.10 (t, 3H).

Example 16

Under a N$_2$ atmosphere, 300 mg (1.11 mmol) of 1-chloro-4-[2-(pyridin-3-yl)-ethyl]-isoquinoline (step 1.6) and 520 mg (3.3 mmol) 4-tert-butyl-cyclohexylamine (cis/trans mixture) are stirred at 120° C. After 2 days, a further 520 mg of 4-tert-butyl-cyclohexylamine are added, followed by 1 g after a total of 4 days. Stirring continues for 3 days at 150° C., then the reaction mixture is cooled to RT and diluted with EtOAc and NaHCO$_3$ solution. The water phase is separated off and extracted twice with EtOAc. The organic phases are washed 3 times with water and brine, dried (Na$_2$SO$_4$) and concentrated by evaporation. Column chromatography (SiO$_2$; toluene/EtOAc 3:1) and elution (toluene/EtOAc 3:1+ 1% Et$_3$N) yields trans 1-(4-tert-butyl-cyclohexylamino)-4-[2-(pyridin-3-yl)-ethyl]-isoquinoline (crystallised from DIPE), followed by cis 1-(4-tert-butyl-cyclohexylamino)-4-[2-(pyridin-3-yl)-ethyl]-isoquinoline. trans derivative: m.p. 124–125° C.; $^1$H NMR (CDCl$_3$) δ8.47 (m, 2H), 7.83 (d, 1H), 7.77 (m, 2H), 7.64 (t, 1H), 7.47 (m, 2H), 7.19 (m, 1H), 4.98 (d, HN), 4.05 (m, 1H), 3.14 (t, 2H), 2.98 (t, 2H), 2.27 (m, 2H), 1.86 (m, 2H), 1.25 (m, 4H), 1.07 (m, 1H), 0.90 (s, 9H). cis derivative: $^1$H NMR (CDCl$_3$) δ8.47 (m, 2H), 7.85 (d, 1H), 7.77 (m, 2H), 7.66 (t, 1H), 7.50 (m, 2H), 7.20 (m, 1H), 5.40 (d, HN), 4.45 (m, 1H), 3.14 (t, 2H), 2.98 (t, 2H), 2.13 (m, 2H), 1.7 (m, 4H), 1.28 (m, 2H), 1.13 (m, 1H), 0.92 (s, 9H).

The following compounds of formula Ia are prepared analogously to the above process (isolated as separated or non-separated isomeric mixtures):

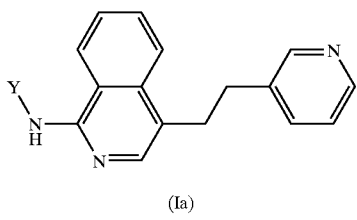

(Ia)

| Ex. | Y—NH | m.p. [° C.] |
|---|---|---|
| 17 | isopropyl-cyclohexyl-NH | 89–92 |
| 17a | isopropyl-cyclohexyl-NH (other isomer) | |
| 18 | ethyl-cyclohexyl-NH | |

Example 19

Under a N$_2$ atmosphere, 600 mg (4.25 mmol) of trans-4-isopropyl-cyclo-hexylamine [for preparation see *Arzneim. Forsch.* 19 (1969), 140] and 120 mg (0.424 mmol) of 1-chloro-4-[2-(6-methyl-pyridin-3-yl)-ethyl]-isoquinoline are heated to 140° C. in an ampulla for 10 h. The reaction mixture is suspended in EtOAc, and mixed with 0.25 ml of NH$_3$ solution (25%) and water. The separated aqueous phase is extracted twice more with EtOAc, the organic phases washed with water and brine, dried (Na$_2$SO$_4$) and concentrated by evaporation. Column chromatography (SiO$_2$; hexane/EtOAc 1:1) yields trans 1-(4-isopropyl-cyclohexylamino)-4-[2-(6-methyl-pyridin-3-yl)-ethyl]-isoquinoline; $^1$H NMR (DMSO-d$_6$) δ8.27 (m, 2H), 7.88 (d, 1H), 7.65 (t, 1H), 7.60 (s, 1H), 7.54 (m, 1H), 7.45 (t, 1H), 7.14 (d, 1H), 6.84 (d, 1H), 3.88 (m, 1H), 3.00 (m, 2H), 2.84 (m, 2H), 2.40 (s, 3H), 2.00 (m, 2H), 1.71 (m, 2H), 1.5–1.0 (m, 6H), 0.86 (d, 6H).

The starting material is prepared as follows:

Step 19.1: 7.0 ml (96 mmol) of SOCl$_2$ are added dropwise, whilst cooling with ice and under a N$_2$ atmosphere, to a solution of 10.75 g (87.3 mmol) of 6-methyl-3-pyridylmethanol [*J. Org. Chem.* 53 (1988), 3513] in 98 ml of dichloromethane. After 1.5 h, the reaction mixture is added to a mixture of 37.4 g (0.13 mol) of Na$_2$CO$_3$.10H$_2$O, 130 ml of ice water and 190 ml of toluene, and stirred for 15 min. The water phase is separated and extracted twice with toluene. The organic phases are dried (Na$_2$SO$_4$) and concentrated by evaporation to half of their volume [→6-methyl-pyridin-3-yl-methylchloride]. 46 g (175 mmol) of triphenylphosphine are added to the resulting solution of 6-methylpyridin-3-yl-methyl chloride in toluene (≈0.2 l) and stirred over night at 80° C. Triphenyl-[(6-methylpyridin-3-yl)-methyl]-phosphonium chloride thereby precipitates and can be filtered off and washed with toluene; $^1$H NMR (DMSO-d$_6$) δi.a. 5.24 (d, J=15.6 Hz, 2H), 2.38 (s, CH$_3$). Further product may be obtained from the above filtrate by stirring at 80° C. for 2–4 days.

Step 19.2: Under a N$_2$ atmosphere, 11.48 g (28.4 mmol) of triphenyl-[(6-methyl-pyridin-3-yl)-methyl]-phosphonium chloride in 218 ml of THF are mixed with 3.34 g (29.7 mmol) of potassium-tert-butylate and stirred for 30 min. The suspension is heated to 50° C. and a mixture of 3.0 g (21.9 mmol) of 1-oxo-1,2-dihydro-isoquinoline-4-carbaldehyde (step 1.3) and 218 ml of THF is added dropwise and finally stirred for 4 h at 60° C. To the cooled reaction mixture is added 170 ml of water and then the THF is evaporated off on a RE. Upon dilution of the residue with water and EtOAc, (E) 4-[2-(6-methyl-pyridin-3-yl)-vinyl]-2H-isochinolin-1-one crystallises and can be filtered off and washed with EtOAc/EtOH 5:1; $^1$H NMR (DMSO-d$_6$) δ11.54 (sb, HN), 8.63 (s, 1H), 8.25 (d, 1H), 8.09 (d, 1H), 8.03 (d, 1H), 7.78 (t, 1H), 7.60 (d, 1H), 7.55 (t, 1H), 7.52 (m, 1H), 7.25 (d, 1H), 7.03 (d, J=16 Hz, 1H), 2.46 (s, H$_3$C). The water phase is separated from the filtrate and extraction effected twice with EtOAc. The organic phases are washed with water and brine, dried (Na$_2$SO$_4$) and concentrated by evaporation. Column chromatography (SiO$_2$, EtOAc→EtOAc/ethanol 20:1→5:1) yields a (E/Z) mixture of 4-[2-(6-methyl-pyridin-3-yl)-vinyl]-2H-isoquinolin-1-one; FAB-MS: (M+H)$^+$=263; HPLC(gradient$_{100}$) $t_{Ret}$=6.7$^Z$/6.9$^E$.

Step 19.3: 3.00 g (11.4 mmol) of an (E/Z) mixture of 4-[2-(6-methyl-pyridin-3-yl)-vinyl]-2H-isoquinolin-1-one in 60 ml of methanol are hydrogenated in the presence of 0.3 g of Pd/C (10%). Filtration through Celite, washing with methanol and concentration by evaporation yield 4-[2-(6-methyl-pyridin-3-yl)-ethyl]-2H-isoquinolin-1-one; $^1$H NMR (DMSO-d$_6$) δ11.09 (sb, HN), 8.27 (s, 1H), 8.22 (d, 1H), 7.82 (d, 1H), 7.75 (t, 1H), 7.52 (m, 2H), 7.14 (d, 1H), 6.89 (s, 1H), 2.91 (m, 2H), 2.83 (m, 2H), 2.40 (s, H$_3$C).

Step 19.4: 3.12 g (11.8 mmol) of 4-[2-(6-methyl-pyridin-3-yl)-ethyl]-2H-isoquinolin-1-one in 48 ml of acetonitrile are mixed, whilst excluding air, with 3.7 ml (40 mmol) of phosphorus oxychloride and 6 ml of 4 N HCl in dioxane and stirred for 18 h at 55° C. After cooling to RT, water/NH$_3$ conc. 10:1 (pH=9) and EtOAc are added, the water phase is separated and extraction effected twice with EtOAc. The organic phases are washed with water and brine, dried (Na$_2$SO$_4$) and concentrated by evaporation to form 1-chloro-4-[2-(6-methyl-pyridin-3-yl)-ethyl]-isoquinoline; $^1$H NMR (DMSO-d$_6$) δ8.3 (m, 3H), 8.09 (s, 1H), 7.94 (t, 1H), 7.83 (t, 1H), 7.56 (d, 1H), 7.15 (d, 1H), 3.30 (t, H$_2$C), 2.94 (t, H$_2$C), 2.40 (s, H$_3$C).

The following compounds of formula Ib are obtained analogously to example 1 by reacting 1-chloro-4-[2-(6-methyl-pyridin-3-yl)-ethyl]-isoquinoline (step 19.1–19.4) with a compound of formula Y—NH$_2$, in which Y is defined as for formula I:

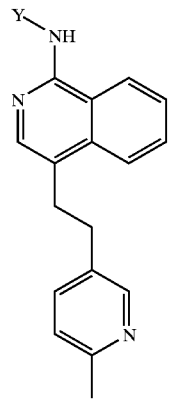

(Ib)

| Ex. | Y—NH | HPLC grad.$_{20-100}$ | m.p. [° C.] |
|---|---|---|---|
| 20 |  | 9.2 | oil |
| 21 |  | 9.1 | 103–105 |
| 22 |  | 9.4 | 195–197 |
| 23 |  |  |  |
| 24 |  |  |  |
| 25 |  |  |  |

Example 26 trans 1-(4-isopropyl-cyclohexylamino)-4-[2-(2-methoxy-pyridin-4-yl)-ethyl]-isoquinoline Preparation is effected analogously to example 19 from trans-4-isopropyl-cyclohexylamine 143 mg (0.478 mmol) of 1-chloro-4-[2-(2-methoxy-pyridin-4-yl)-ethyl]-isoquinoline; FAB-MS: M+H)$^+$=404.

The starting material is prepared as follows:

Step 26.1: 1.57 ml (21.6 mmol) of SOCl$_2$ are added dropwise, whilst cooling with ice and under a N$_2$ atmosphere, to a solution of 1.5 g (10.8 mmol) of 2-methoxy-4-(hydroxymethyl)-pyridine [for preparation see J. Org. Chem. 54 (1989), 5580] in 13 ml of chloroform. After 16 h at RT, the mixture is concentrated by evaporation, water and 2N sodium hydroxide solution are added to the residue, and extraction immediately takes place 3 times with chloroform. The organic phases are washed with water and brine, dried (Na$_2$SO$_4$) and concentrated by evaporation to form 2-methoxy-pyridin-4-yl-methylchloride; $^1$H NMR (CDCl$_3$) δ8.15 (d, 1H), 6.90 (d, 1H), 6.76 (s, 1H), 4.49 (s, 2H), 3.94 (s, H$_3$C).

Step 26.2: A solution of 1.46 g (9.26 mmol) of 2-methoxy-pyridin-4-yl-methyl chloride and 4.85 g (18.5 mmol) of triphenylphosphine in 27 ml of toluene is stirred under reflux for 24 h whilst excluding air. Triphenyl-(2-methoxy-pyridin-4-yl)-methyl]-phosphonium chloride thereby precipitates, and can be filtered off and washed with toluene; $^1$H NMR (DMSO-d$_6$) δ7.85 (m, 7H), 7.74 (m, 3H), 7.61 (m, 6H), 6.79 (m, 1H), 6.48 (s, 1H), 5.73 (d, J=15.6 Hz, 2H), 3.77 (s, CH$_3$).

Further product may be obtained from the above filtrate by boiling for a longer time (2–4 days).

Step 26.3: Under a $N_2$ atmosphere, 1.07 g (2.55 mmol) of triphenyl-[(2-methoxy-pyridin-4-yl)-methyl]-phosphonium chloride in 20 ml of THF are mixed with 388 mg (3.46 mmol) of potassium-tert-butylate and stirred for 30 min. The suspension is heated to 50° C., and a mixture of 485 mg (2.80 mmol) of 1-oxo-1,2-dihydro-isoquinoline-4-carbaldehyde (step 1.3) and 20 ml of THF is added dropwise, and the yellow solution is finally stirred for 4 h at 60° C., thereby forming a suspension once more. This is diluted with water and EtOAc, and the water phase separated and extraction carried out with 2 portions of EtOAc. The organic phases are washed twice with water and brine, dried ($Na_2SO_4$) and concentrated by evaporation. Column chromatography ($SiO_2$, EtOAc/toluene 1:1) yields a (E/Z) mixture of 4-[2-(2-methoxy-pyridin-4-yl)-vinyl]-2H-isoquinolin-1-one contaminated with triphenyl-phosphine oxide; HPLC(gradient$_{20-100}$) $t_{Ret}$=8.4/8.6.

Step 26.4: 1.1 g of the above (E/Z) mixture of 4-[2-(2-methoxy-pyridin-4-yl)-vinyl-2H-isoquinolin-1-one in 20 ml of methanol are hydrogenated in the presence of 0.6 g of Pd/C (10%). Filtration through Celite, washing with a lot of methanol, concentrating by evaporation and column chromatography ($SiO_2$, methylene chloride/acetone 3:1→acetone) yield 4-[2-(2-methoxy-pyridin-4-yl)-ethyl]-2H-isoquinolin-1-one; $^1$H NMR (DMSO-$d_6$) δ11.10 (sb, HN), 8.22 (d, 1H), 8.03 (d, 1H), 7.81 (d, 1H), 7.75 (t, 1H), 7.50 (t, 1H), 6.92 (m, 1H), 6.88 (d, 1H), 6.70 (s, 1H), 3.80 (s, $H_3C$), 2.93 (m, 2H), 2.84 (m, 2H).

Step 26.5: Under a $N_2$ atmosphere, 160 mg (0.57 mmol) of 4-[2-(2-methoxy-pyridin-4-yl)-ethyl]-2H-isoquinolin-1-one in 3.7 ml of acetonitrile are mixed with 131 μl (1.43 mmol) of phosphorus oxychloride and 0.28 ml of 4 N HCl in dioxane and stirred for 7 h at 65° C. After cooling to RT, water/$NH_3$ conc. 10:1 and EtOAc are added, the water phase is separated and extraction effected twice with EtOAc. The organic phases are washed with water and brine, dried ($Na_2SO_4$) and concentrated by evaporation to form 1-chloro-4-[2-(2-methoxy-pyridin-4-yl)-ethyl]-isoquinoline; $^1$H NMR (DMSO-$d_6$) δ8.30 (d, 1H), 8.27 (d, 1H), 8.13 (s, 1H), 8.03 (d, 1H), 7.94 (t, 1H), 7.85 (t, 1H), 6.90 (d, 1H), 6.73 (s, 1H), 3.80 (s, $H_3C$), 3.32 (t, $H_2C$), 2.95 (t, $H_2C$).

Example 27

Analogously to example 29, 70 mg (0.17 mmol) of trans-1-(4-isopropyl-cyclohexylamino)-4-[2-(2-methoxy-pyridin-4-yl)-ethyl]-isoquinoline in 1 ml of chloroform are reacted with 46 μl (0.34 mmol) of trimethylsilyl iodide, and trans-1-(4-isopropyl-cyclohexylamino)-4-[2-(2-hydroxy-pyridin-4-yl)-ethyl]-isoquinoline is obtained from the crude product by means of medium-pressure chromatography ($CH_3CN/H_2O$/a little TFA; fractions containing the product are neutralised with $NH_3$, partially evaporated and extracted with EtOAc); FAB-MS: $(M+H)^+$=390.

Example 28 trans 1-(4-isopropyl-cyclohexylamino)-4-[6-(methoxy-pyridin-3-yl)-methyl]-isoquinoline Preparation is effected analogously to example 19 from trans-4-isopropyl-cyclohexylamine and 1-chloro-4-[6-(2-methoxy-pyridin-3-yl)-methyl]-isoquinoline; FAB-MS: $(M+H)^+$=390; TLC(acetone/$CH_2Cl_2$ 1:19): $R_f$=0.13.

The starting material is prepared as follows:

Step 28.1: A solution of 3.12 g (19.8 mmol) of 2-methoxy-5-chloromethylpyridine [for preparation see *Drug Des. Disc.* 10 (1993), 35] and 5.72 g (21.8 mmol) of triphenylphosphine in 50 ml of toluene is stirred under reflux for 3 days whilst excluding air.

Triphenyl-[(6-methoxy-pyridin-3-yl)-methyl]-phosphonium chloride thereby precipitates and can be filtered off and washed with toluene; m.p. 259–260° C. Further product may be obtained from the above filtrate by boiling for a longer time. Formation of the product can be accelerated by working in boiling xylene instead of toluene.

Step 28.2: Under a $N_2$ atmosphere, an ice-cooled suspension of 6.19 g (14.7 mmol) of triphenyl-[(6-methoxy-pyridin-3-yl)-methyl]-phosphonium chloride in 50 ml of THF is mixed with a solution of 2.20 g (18 mmol) of potassium-tert-butylate in 50 ml of THF and stirred at RT for 30 min. Then, whilst cooling with ice, 2.7 g (17 mmol) of (2-oxo-ethyl)-carbamic acid-tert-butylester (Aldrich) in 50 ml of THF is added dropwise to the yellow-red solution and stirred for 1 h at RT. The yellow solution is diluted with water and EtOAc, and the water phase separated and extraction effected with 2 portions of EtOAc. The organic phases are washed twice with water and brine, dried ($Na_2SO_4$) and concentrated by evaporation. Column chromatography ($SiO_2$, hexane/diethylether 4:1) yields (Z) [3-(6-methoxy-pyridin-3-yl)-allyl]-carbamic acid-tert-butylester, followed by (E) [3-(6-methoxy-pyridin-3-yl)-allyl]-carbamic acid-tert-butylester. (Z)-isomer: m.p. 51° C. (E)-isomer: m.p. 91° C.

Step 28.3: 2.57 g (9.7 mmol) of an (E/Z) mixture of [3-(6-methoxy-pyridin-3-yl)-allyl]-carbamic acid-tert-butyl ester in 20 ml of formic acid are stirred whilst excluding air. After 16 h, the brown solution is lyophilised and the residue taken up in diethylether and diluted $Na_2CO_3$ solution. The separated water phase is extracted a further 4 times with EtOAc. The organic phases are washed with dil. $Na_2CO_3$ solution, water and brine, dried ($Na_2SO_4$) and concentrated by evaporation to form an (E/Z) mixture of 3-(6-methoxy-pyridin-3-yl)-allylamine (E/Z=11:8); $^1$H NMR (CDCl$_3$) δi.a. 6.44 (d, J=16 Hz, 1H$^E$), 6.33 (d, J=11.6 Hz, 1H$^Z$).

Step 28.4: Under a $N_2$ atmosphere, 2.96 g (11.1 mmol) of 2-iodo-benzoyl chloride in 8 ml of acetonitrile are added dropwise to an ice-cooled solution of 1.59 g (9.7 mmol) of (E/Z) 3-(6-methoxy-pyridin-3-yl)-allylamine and 1.7 ml (15.4 mol) of 4-methylmorpholine in 8 ml of acetonitrile. After stirring for 3 h at RT, the suspension is diluted with 50 ml of water, 10 ml of sat. $Na_2CO_3$ solution and 50 ml of EtOAc. The biphasic suspension is stirred for 1 h, filtered and washed with water and EtOAc (→2-iodo-benzoic acid-[3-(6-methoxy-pyridin-3-yl)-allylamide]: E/Z=2:1). The water phase is separated from the filtrate and extraction effected twice with EtOAc. The organic phases are washed twice with water and brine, dried ($Na_2SO_4$) and concentrated by evaporation. Column chromatography ($SiO_2$, toluene/EtOAc 2:1) yields (Z) 2-iodo-benzoic acid-[3-(6-methoxy-pyridin-3-yl)-allylamide], followed by (E) 2-iodo-benzoic acid-[3-(6-methoxy-pyridin-3-yl)-allylamide]. (Z)-isomer: m.p. 133° C. (E)-isomer: m.p. 142–143° C.

Step 28.5: Under a $N_2$ atmosphere, 2.04 g (5.17 mmol) of an (E/Z) mixture of 2-iodo-benzoic acid-[3-(6-methoxy-pyridin-3-yl)-allylamide], 1.53 g (5.17 mmol) of tetrabutylammonium chloride and 22 mg (0.1 mmol) of palladium diacetate are dissolved in 80 ml of DMF, then 1.8 ml (12.9 mmol) of triethylamine are added and stirring effected for 2 days at 110° C. Filtration is carried out, and the DMF is partially evaporated on a RE. The residue is dissolved with EtOAc and diluted $Na_2CO_3$ solution, the water phase separated and extraction effected twice more with EtOAc. The organic phases are washed twice with water and brine, dried (Na₂SO₄) and concentrated by evaporation. Column chromatography (SiO₂, methylene chloride/acetone 3:1), concentration by evaporation and stirring in petroleum ether yield 4-[(6-methoxy-pyridin-3-yl)-methyl]-2H-isoquinolin-1-one; m.p. 191° C.; HPLC(gradient$_{20-100}$) $t_{Ret}$=7.9.

Step 28.6: 1-Chloro-4-[6-(methoxy-pyridin-3-yl)-methyl]-isoquinoline is obtained analogously to step 26.5 from 4-[(6-methoxy-pyridin-3-yl)-methyl]-2H-isoquinolin-1-one; HPLC(gradient$_{20-100}$) $t_{Ret}$=13.0.

Example 29

Under a N₂ atmosphere, 122 µl (0.90 mmol) of trimethylsilyl iodide are added to a solution of 351 mg (0.90 mmol) of trans 1-(4-isopropyl-cyclohexylamino)-4-[(6-methoxy-pyridin-3-yl)-methyl]-isoquinoline in 8 ml of chloroform, and stirred for 14 h at 60° C., then a further 122 µl of trimethylsilyl iodide are added and stirring is again effected for 3 h at 60° C. The mixture is cooled, the supernatant solution decanted from the solid, rinsed with a little chloroform and the chloroform phases discarded. The residue is dissolved by stirring in 40 ml of methylene chloride, 10 ml of methanol, 5 ml of EtOAc, 5 ml of saturated NaHCO₃ solution and 5 ml of water. After adding more water, the organic phase is separated and washed with water and brine. The aqueous phases are extracted 3 more times with EtOAc. Drying (Na₂SO₄), concentrating by evaporation and crystallisation from hexane yield trans 1-(4-isopropyl-cyclohexylamino)-4-[(6-hydroxy-pyridin-3-yl)-methyl]-isoquinoline from the organic phases; FAB-MS: (M+H)⁺= 376; TLC(acetone/CH₂Cl₂ 3:2): $R_f$=0.13.

Example 30

The following compounds of formula I are obtained analogously to the processes described in this text from 4-isopropyl-3-methylcyclohexylamine, which is prepared by hydrogenation of 4-isopropyl-3-methylaniline, or from 3-amino-isoquinoline:

a) 1-(4-isopropyl-3-methylcyclohexylamino)-4-[6-(methoxy-pyridin-3-yl)-methyl]-isoquinoline;
b) 1-(4-isopropyl-3-methylcyclohexylamino)-4-[6-(hydroxy-pyridin-3-yl)-methyl]-isoquinoline;
c) 1-(isoquinolin-3-yl-amino)-4-[2-(6-methoxy-pyridin-3-yl)-ethyl]-isoquinoline;
d) 1-(isoquinolin-3-yl-amino)-4-[2-(6-hydroxy-pyridin-3-yl)-ethyl]-isoquinoline.

Examples 31 and 32

The following compounds of formula Ic are obtained analogously to example 1 (optionally after chromatography on SiO₂) by reacting 1-chloro-4-[2-(2-methoxy-pyridin-4-yl)-ethyl]-isoquinoline (step 26.1–26.5) with a compound of formula Y—NH₂, in which Y is defined as for formula I. From these, the following compounds of formula Id are obtained (optionally after chromatography on SiO₂) analogously to the described processes (1. Me₃SiI/CHCl₃, 2. hydrolysis):

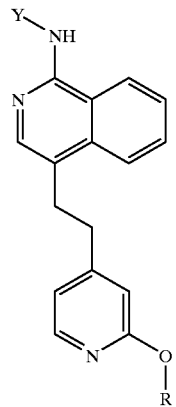

R = Me: (Ic)
R = H: (Id)

| Ex. | Y—NH | R | HPLC grad.$_{20-100}$ | FAB-MS (M+H)⁺ | m.p. [° C.] |
|---|---|---|---|---|---|
| 31a | ![Br-ethylphenyl] | Me | 11.3 | 462/464 | |
| 32a | | H | 10.7 | 448/450 | |
| 31b | ![isopropyl-methylphenyl] | Me | | | |
| 32b | | H | | | |
| 31c | ![Cl-CF3-phenyl] | Me | | | |
| 32c | | H | | | |
| 31d | ![CF3-phenyl] | Me | 10.2 | 424 | oil |
| 32d | | H | 9.5 | 410 | |
| 31e | ![tBu-phenyl] | Me | 11.6 | 412 | |
| 32e | | H | 10.9 | 398 | |
| 31f | ![CF3-methylphenyl] | Me | 10.7 | 438 | 155–157 |
| 32f | | H | 9.9 | 424 | |

Examples 33 and 34

The following compounds of formula Ie are obtained analogously to example 1 (optionally after chromatography on SiO$_2$) by reacting 1-chloro-4-[(6-methoxy-pyridin-3-yl)-methyl]-isoquinoline (step 28.1–28.6) with a compound of formula Y—NH$_2$, in which Y is defined as for formula I. From these, the following compounds of formula If are obtained (optionally after chromatography) analogously to the described processes (1. Me$_3$SiI/CHCl$_3$, 2. hydrolysis):

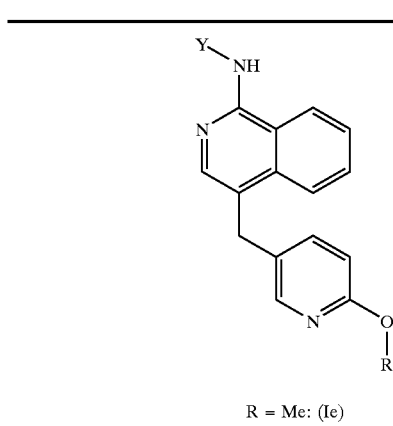

R = Me: (Ie)
R = H: (If)

| Ex. | Y—NH | R | HPLC grad.$_{20-100}$ | FAB-MS (M + H)$^+$ | m.p. [° C.] |
|---|---|---|---|---|---|
| 33a | 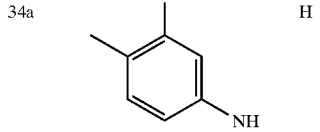 | Me | | | |
| 34a | | H | | | |
| 33b* | 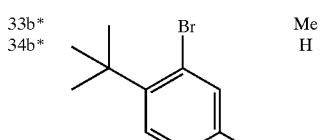 | Me | | | |
| 34b* | | H | | | |
| 33c |  | Me | | | |
| 34c | | H | | | |
| 33d | 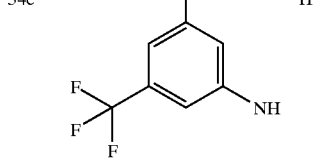 | Me | | | |
| 34d | | H | | | |

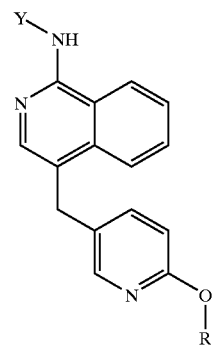

R = Me: (Ie)
R = H: (If)

| Ex. | Y—NH | R | HPLC grad.$_{20-100}$ | FAB-MS (M + H)$^+$ | m.p. [° C.] |
|---|---|---|---|---|---|
| 33e |  | Me | 12.3 | 398 | 134–136 |
| 34e | | H | 10.3 | 384 | |
| 33f | 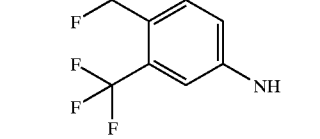 | Me | 10.9 | 410 | 113–114 |
| 34f | | H | 9.0 | 396 | |
| 33g | 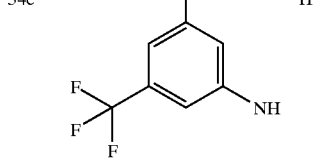 | Me | 12.1 | 448/450 | 110–113 |
| 34g | | H | 10.0 | 434/436 | 232–234 |

*The starting material is prepared as follows: For examples 33b and 34b: 3-bromo-4-(tert-butyl)-aniline is obtained by hydrogenation of 3-bromo-4-(tert-butyl)-nitrobenzene (Maybridge).

Example 35

Under a N$_2$ atmosphere, 150 mg (0.334 mmol) of 1-(3-bromo-4-ethyl-anilino)-4-[2-(2-hydroxpyridin-4-yl)-ethyl]-isoquinoline (Ex. 32a) in 5 ml of acetonitrile are mixed with 76 μl (0.83 mmol) of phosphorus oxychloride and 0.17 ml (0.68 mmol) of 4 N HCl in dioxane, and stirred at 65° C. A further 76 μl of phosphorus oxychloride is added after 12 h, and stirring continues for 48 h at 65° C. The mixture is cooled to RT, 4 ml of 10% NH$_3$ solution added, and it is partitioned between 3 portions of EtOAc, 2 portions of water and brine. Drying (Na$_2$SO$_4$), concentrating by evaporation and chromatography on silica gel (acetone/methylene chloride 3:2) yield 1-(3-bromo-4-ethyl-anilino)-4-[2-(2-chloro-pyridin-4-yl)-ethyl]-isoquinoline; FAB-MS: (M+H)$^+$=466/468; HPLC(gradient$_{20-100}$) t$_{Ret}$=13.4.

Examples 36a. 36b and 36c

Under a N$_2$ atmosphere, 146 mg (0.5 mmol) of 5-chloro-8-[(6-methoxy-pyridin-3-yl)-methyl]-[1,6]naphthyridine (contains a little 5-chloro-8-[(6-chloro-pyridin-3-yl)-methyl]-[1,6]naphthyridine as an impurity) in 2.0 ml of tbutanol/dioxane 1:5 are mixed with 160 mg (1 mmol) of 3-trifluoromethyl-aniline and 0.12 ml of 4 N HCl/dioxane and stirred for 14 h at 70° C. The cooled reaction mixture is dissolved in diluted $Na_2CO_3$ solution and EtOAc whilst adding ethanol. The water phase is separated and extracted twice with EtOAc. The organic phases are dried ($Na_2SO_4$) and concentrated by evaporation. The resulting oil is separated by reversed phase medium-pressure chromatography (water/-acetonitrile/TFA). The fractions are partially concentrated by evaporation, then solid $NaHCO_3$ is added to the aqueous residue. Extraction with 3 portions of EtOAc, drying ($Na_2SO_4$) and concentration by evaporation yields 5-(3-trifluoromethyl-anilino)-8-[(6-hydroxy-pyridin-3-yl)-methyl]-[1,6]naphthyridine 36a (FAB-MS: $(M+H)^+=397$; HPLC(gradient$_{20-100}$) $t_{Ret}=8.5$); 5-(3-trifluoromethyl-anilino)-8-[(6-methoxy-pyridin-3-yl)-methyl]-[1,6] naphthyridine 36b (FAB-MS: $(M+H)^+=411$; HPLC (gradient$_{20-100}$) $t_{Ret}=10.0$) and 5-(3-trifluoromethyl-anilino)-8-[(6-chloro-pyridin-3-yl)-methyl]-[1,6] naphthyridine 36c (FAB-MS: $(M+H)^+=415$; HPLC (gradient$_{20-100}$) $t_{Ret}=1.5$).

Alternative Preparation of 5-(3-trifluoromethyl-anilino)-8-[(6-hydroxy-pyridin-3-yl)-methyl]-[1,6]naphthyridine: 41 mg (0.10 mmol) of 5-(3-trifluoromethyl-anilino)-8-[(6-methoxy-pyridin-3-yl)-methyl]-[1,6]naphthyridine are dissolved in 2.5 ml of chloroform whilst excluding moisture in an ampulla, then 0.2 ml (1.4 mmol) of $Me_3SiI$ are added and the mixture is stirred for 16 h at 70° C. After cooling, 5 ml of saturated $NaHCO_3$ solution, 5 ml of water and 20 ml of EtOAc are added, and stirring is effected until everything has dissolved. Then dil. $Na_2CO_3$ solution and EtOAc are added to the solution, the aqueous phase is separated and extracted twice more with EtOAc. The organic phases are washed with water and brine, dried ($Na_2SO_4$), concentrated by evaporation and purified to the title compound as above by means of reversed phase medium-pressure chromatography (water/acetonitrile/TFA).

The starting material is prepared as follows:

Step 36.1: Under a $N_2$ atmosphere, 10.37 g (59 mmol) of 2-chloronicotinic acid chloride and 8.85 ml (80 mol) of 4-methylmorpholine are dissolved in 44 ml of acetonitrile, cooled to −40° C., and a solution of 8.8 g (53.6 mmol) of (E/Z) 3-(6-methoxy-pyridin-3-yl)-allylamine (step 28.3) in 44 ml of acetonitrile is added dropwise. A thick yellow suspension is immediately formed. After stirring for 30 min, the suspension is diluted with 220 ml of water and 52 ml of saturated $Na_2CO_3$ solution, stirred for 10 min, filtered and the crystallisate washed with water and hexane/diethylether. This yields a 4:1 mixture of the double bond isomers of 2-chloro-N-[3-(6-methoxy-pyridin-3-yl)-allyl]-nicotinamide; FAB-MS: $(M+H)^+=304$; HPLC(gradient$_{20-100}$) $t_{Ret}=7.7/8.2$. Extraction of the filtrate with EtOAc and column chromatography ($SiO_2$, hexane/EtOAc 1:3) yield further product.

Step 36.2: Under a $N_2$ atmosphere, 1.02 g (3.36 mmol) of an (E/Z) mixture of 2-chloro-N-[3-(6-methoxy-pyridin-3-yl)-allyl]-nicotinamide, 995 mg (3.36 mmol) of tetrabutylammonium chloride, 1240 mg (3.36 mmol) of tetrabutylammonium iodide and 80 mg (0.36 mmol) of palladium diacetate are dissolved in 63 ml of DMF, then 1.2 ml (8.6 mmol) of triethylamine are added and stirring effected for 28 h at 150° C. in an ampulla. After adding a further 80 mg of palladium diacetate, stirring is again effected for 24 h at 150° C. The mixture is filtered and the DMF is partially evaporated on a RE. The residue is dissolved with EtOAc and diluted $Na_2CO_3$ solution, the water phase separated and extraction effected twice more with EtOAc/EtOH 9:1. The organic phases are washed with water and brine, dried ($Na_2SO_4$) and concentrated by evaporation. Column chromatography ($SiO_2$, methylene chloride/EtOAc 1:1→EtOAc) yields 8-[(6-methoxy-pyridin-3-yl)-methyl]-6H-[1,6] naphthyridin-5-one A (contaminated with ca. 25% 8-[1-(6-methoxy-pyridin-3-yl)-methylidene]-7,8-dihydro-6H-[1,6] naphthyridin-5-one B); FAB-MS: $(M+H)^+=268$; HPLC (gradient$_{20-100}$) $t_{Ret}=6.0/8.3$; $^1H$ NMR ($CDCl_3$) i.a. δ4.12 (s, $H_2C$—$C(8)$ of A), 4.71 (d, 2.3 Hz, $H_2C(7)$ of B).

Step 36.3: 396 mg (1.48 mmol) of 8-[(6-methoxy-pyridin-3-yl)-methyl]-6H-[1,6]naphthyridin-5-one in 24 ml of acetonitrile are mixed, whilst excluding air, with 1.4 ml (15 mmol) of phosphorus oxychloride and 0.78 ml of 4 N HCl in dioxane and stirred for 96 h at 65° C. After cooling to RT, partial concentration by evaporation takes place on a RE, then 40 ml of ice water and 10 ml of $NH_3$ solution are added and extraction carried out 3 times with EtOAc. The organic phases are washed with water and brine, dried ($Na_2SO_4$) and concentrated by evaporation to form 5-chloro-8-[(6-methoxy-pyridin-3-yl)-methyl]-[1,6]naphthyridine (contaminated with a little 5-chloro-8-[(6-chloro-pyridin-3-yl)-methyl]-[1,6]naphthyridine); FAB-MS: $(M+H)^+=286$; HPLC(gradient$_{20-100}$) $t_{Ret}=10.2$.

Examples 37a and 37b

Under a $N_2$ atmosphere, 241 mg (0.84 mmol) of 5-chloro-8-[(6-methoxy-pyridin-3-yl)-methyl]-[1,6]naphthyridine in 4 ml of methanol are mixed with 252 mg (1.26 mmol) of 3-bromo-4-ethyl-aniline (Ex. 9) and 0.21 ml of 4 N HCl/dioxane and stirred for 16 h at 80° C. The cooled reaction mixture is taken up with diluted $Na_2CO_3$ solution and EtOAc. The water phase is separated and extracted twice with EtOAc. The organic phases are dried (Na2SO$_4$) and concentrated by evaporation. Column chromatography ($SiO_2$, toluene/EtOAc 2:1→EtOAc/acetone/EtOH 4:4:1→acetone/EtOH 9:1) and crystallisation from hexane yield 5-(3-bromo-4-ethyl-anilino)-8-[(6-methoxy-pyridin-3-yl)-methyl]-[1,6]naphthyridine 37a (m.p. 142–146° C.; FAB-MS: $(M+H)^+=449/451$; HPLC(gradient$_{20-100}$) $t_{Ret}=10.9$) and 5-(3-bromo-4-ethyl-anilino)-8-[(6-hydroxy-pyridin-3-yl)-methyl]-[1,6]naphthyridine 37b (m.p. 262–265° C.; FAB-MS: $(M+H)^+=435/437$; HPLC (gradient$_{20-100}$) $t_{Ret}=9.3$).

Example 38 trans 5-(4-isopropyl-cyclohexylamino)-8-[6-(methoxy-pyridin-3yl)-methyl]-[1,6]naphthyridine Preparation is effected analogously to example 19 from 1.9 g (13 mmol) of trans-4-isopropyl-cyclohexylamine and 770 mg (2.69 mmol) of 5-chloro-8-[(6-methoxy-pyridin-3-yl)-methyl]-[1,6]naphthyridine; m.p. 142–144° C; FAB-MS: $(M+H)^+=391$.

Example 39

Under a $N_2$ atmosphere, 142 μl (1.02 mmol) of trimethylsilyl iodide are added to 400 mg (1.02 mmol) of trans 5-(4-isopropyl-cyclohexylamino)-8-[(6-methoxy-pyridin-3-yl)-methyl]-[1,6]naphthyridine in 7 ml of chloroform, and stirring is effected for 12 h at 70° C. The mixture is cooled, EtOAc and diluted $NaHCO_3$ are added, stirring is effected until everything has dissolved, the organic phase is separated and washed with water and brine. The aqueous phases are extracted twice more with EtOAc. Drying ($Na_2SO_4$), concentrating by evaporation, column chromatography ($SiO_2$, EtOAc/EtOH 5:1) and stirring with DIPE yield trans 5-(4- isopropyl-cyclohexylamino)-8-[(6-hydroxy-pyridin-3-yl)-methyl]-[1,6]naphthyridine; m.p. 232–235° C.; FAB-MS: (M+H)⁺=377.

Examples 40 and 41

The following compounds of formula Ig are obtained analogously to the above examples (optionally after chromatography on SiO₂) by reacting 5-chloro-8-[(6-methoxy-pyridin-3-yl)-methyl]-[1,6]naphthyridine (step 36.1–36.3) with a compound of formula Y—NH₂, in which Y is defined as for formula I. From these, the following compounds of formula Ih are obtained (optionally after chromatography on SiO₂) analogously to the above examples:

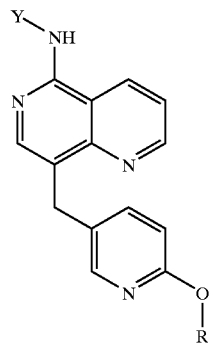

R = Me: (Ig)
R = H: (Ih)

| Ex. | Y—NH | R | HPLC grad.$_{20-100}$ | FAB-MS (M+H)⁺ | m.p. [° C.] |
|---|---|---|---|---|---|
| 40a 41a | Br-methylphenyl-NH | Me H | | | |
| 40b 41b | t-Bu,Br-phenyl-NH | Me H | | | |
| 40c 41c | Cl,CF₃-phenyl-NH | Me H | | | |
| 40d 41d | bis-CF₃-phenyl-NH | Me H | | | |
| 40e 41e | 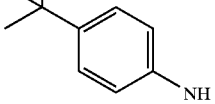 | Me H | 10.4 9.3 | 399 385 | 173–175 |
| 40f 41f | 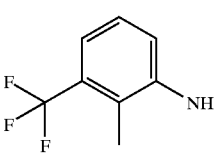 | Me H | 10.2 8.2 | 429 415 | 126–127 205–208 |
| 40g 41g | 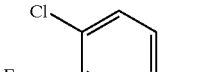 | Me H | | | |
| 40h 41h | 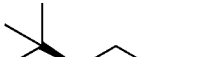 | Me H | 11.7 9.8 | 445 431 | 180–182 |
| 40i 41i | t-Bu-cyclohexyl-NH | Me H | | | |
| 40j 41j | 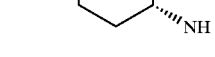 | Me H* | | | |

*5-[5-(2-Isopropyl-[1,3]dioxan-5-ylamino)-[1,6]naphthyridin-8-ylmethyl]-1.H.-pyridin-2-one can be prepared via a route similar as described in Example 49.

Examples 42, 43 and 44

The following compounds of formulae Ii, Ij and Ik are obtained from 4-chloro-pyrimidine-5-carboxylic acid chloride analogously to i.a. example 36:

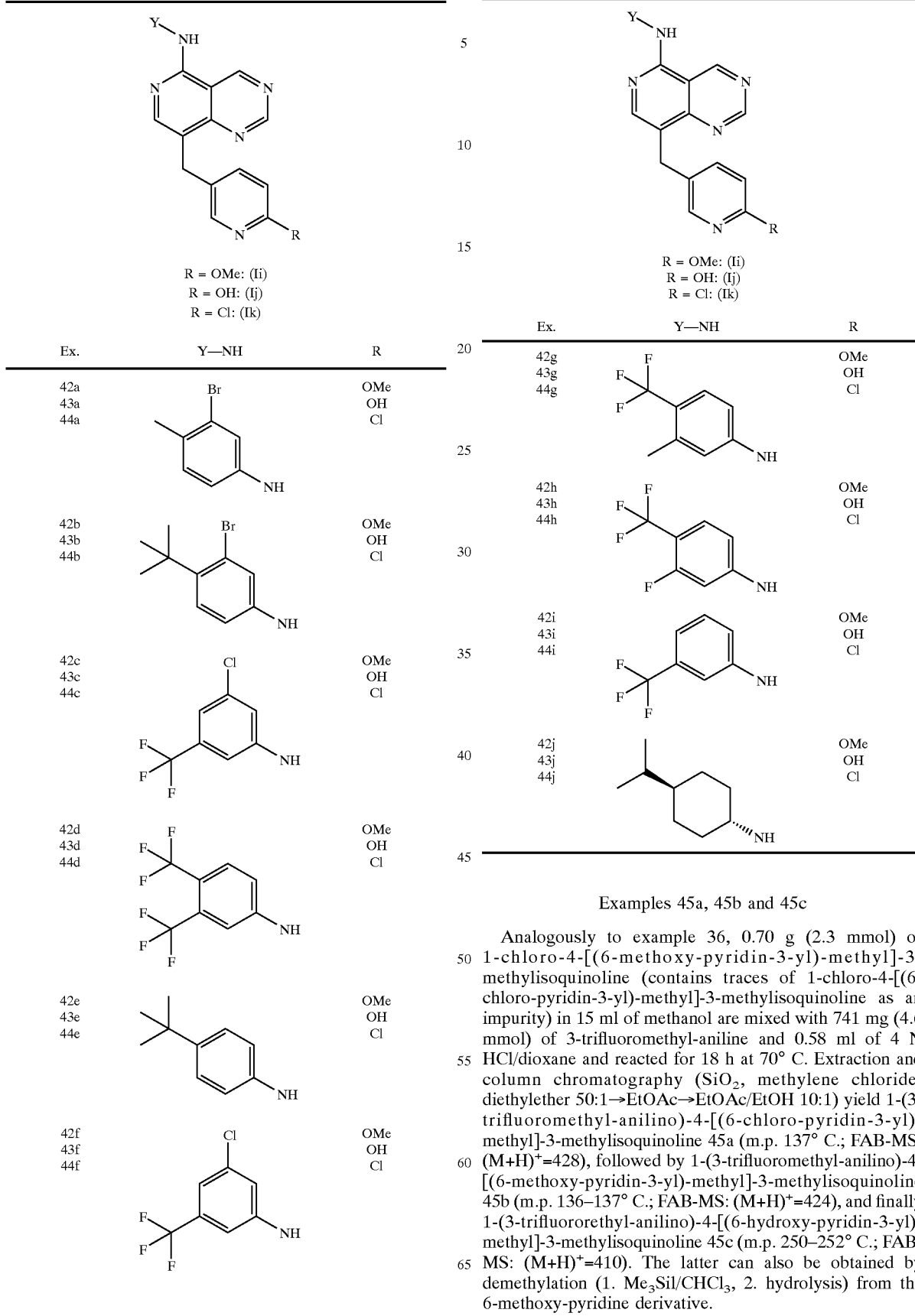

Examples 45a, 45b and 45c

Analogously to example 36, 0.70 g (2.3 mmol) of 1-chloro-4-[(6-methoxy-pyridin-3-yl)-methyl]-3-methylisoquinoline (contains traces of 1-chloro-4-[(6-chloro-pyridin-3-yl)-methyl]-3-methylisoquinoline as an impurity) in 15 ml of methanol are mixed with 741 mg (4.6 mmol) of 3-trifluoromethyl-aniline and 0.58 ml of 4 N HCl/dioxane and reacted for 18 h at 70° C. Extraction and column chromatography (SiO$_2$, methylene chloride/diethylether 50:1→EtOAc→EtOAc/EtOH 10:1) yield 1-(3-trifluoromethyl-anilino)-4-[(6-chloro-pyridin-3-yl)-methyl]-3-methylisoquinoline 45a (m.p. 137° C.; FAB-MS: (M+H)$^+$=428), followed by 1-(3-trifluoromethyl-anilino)-4-[(6-methoxy-pyridin-3-yl)-methyl]-3-methylisoquinoline 45b (m.p. 136–137° C.; FAB-MS: (M+H)$^+$=424), and finally 1-(3-trifluororethyl-anilino)-4-[(6-hydroxy-pyridin-3-yl)-methyl]-3-methylisoquinoline 45c (m.p. 250–252° C.; FAB-MS: (M+H)$^+$=410). The latter can also be obtained by demethylation (1. Me$_3$SiI/CHCl$_3$, 2. hydrolysis) from the 6-methoxy-pyridine derivative.

The starting material is prepared as follows:

Step 45.1: Under a $N_2$ atmosphere, 82.9 g (0.60 mol) of $K_2CO_3$ are added to an ice-cooled solution of 21.06 g (0.28 mol) of rac. 2-amino-1-propanol in 310 ml of dioxane/water 1:1, and then a solution of 50 g (187 mmol) of 2-iodobenzoyl chloride in 310 ml of dioxane is added dropwise. After stirring for 2 h at RT, the solution is diluted with EtOAc and 5% citric acid, the water phase is separated and extracted twice more with EtOAc. The organic phases are washed with water, $NaHCO_3$ solution, water and brine, dried ($Na_2SO_4$) and concentrated by evaporation. By adding hexane, rac. 2-iodo-benzoic acid-(1-hydroxy-prop-2-yl-amide) starts to crystallise; m.p. 84–86° C.

Step 45.2: A solution of 54.9 g (345 mmol) of sulfur trioxide-pyridine complex in 150 ml of DMSO is added dropwise at RT to 35 g (115 mmol) of rac. 2-iodo-benzoic acid-(1-hydroxy-prop-2-yl-amide) in 50 ml of DMSO and 48 ml (345 mmol) of triethylamine. After 10 min, the mixture is poured onto 0.4 l of EtOAc, 0.2 l of sat. $NaHCO_3$ solution and 0.2 l of water, the aqueous phase is separated and extracted 4 more times with EtOAc. The organic phases are washed with water and brine, dried ($Na_2SO_4$) and concentrated by evaporation to form rac. 2-iodo-benzoic acid-(1-oxo-prop-2-yl-amide).

Step 45.3: Under a $N_2$ atmosphere, an ice-cooled suspension of 42 g (100 mmol) of triphenyl-[(6-methoxy-pyridin-3-yl)-methyl]-phosphonium chloride (Ex. 28.1) in 270 ml of THF is mixed with a solution of 13.4 g (110 mmol) of potassium-tert-butylate in 270 ml of THF and stirred at RT for 30 min. Subsequently, 29.4 g (97 mmol) of rac. 2-iodo-benzoic acid-(1-oxo-prop-2-yl-amide) in 270 ml of THF is added dropwise to the yellow-red solution and stirred for 0.5 h. The mixture is partially concentrated by evaporation on a RE and the residue is diluted in EtOAc and water. The water phase is separated, extracted twice with EtOAc and discarded. The organic phases are washed twice with water and then extracted with 400 ml of 2N HCl and with 2 portions of 100 ml 1N HCl. The acidic aqueous extracts are collected in a solution of 138 g of $K_2CO_3$ in 0.5 l of water. An oil is thereby secreted and crystallises when left to stand. Filtering by suction, washing with water and recrystallising from 50 ml of boiling acetonitrile yields rac. trans 2-iodo-benzoic acid-[1-methyl-3-(6-methoxy-pyridin-3-yl)-allylamide] (m.p. 132° C.; FAB-MS: $(M+H)^+$=409; TLC(hexane/EtOAc 1:1): $R_f$=0.42). The EtOAc phases extracted with aqueous HCl contain further product. For this reason, they are washed with sat. $Na_2CO_3$ solution and brine, dried ($Na_2SO_4$) and concentrated by evaporation. Column chromatography ($SiO_2$, hexane/EtOAc 2:1→3:2) and crystallisation from hot acetonitrile yields rac. cis 2-iodo-benzoic acid-[1-methyl-3-(6-methoxy-pyridin-3-yl)-allylamide](m.p. 145–147° C.; FAB-MS: $(M+H)^+$=409; TLC(hexane/EtOAc 1:1): $R_f$=0.51).

Step 45.4: Under a $N_2$ atmosphere, 8 g (19 mmol) of an (E/Z) mixture of rac. 2-iodo-benzoic acid-[1-methyl-3-(6-methoxy-pyridin-3-yl)-allylamide], 5.9 g (19 mmol) of tetrabutylammonium chloride and 0.12 g of palladium diacetate are dissolved in 170 ml of DMF, then 8.9 g (48 mmol) of tributylamine are added and stirred for 20 h at 150° C. The mixture is filtered and the DMF is partially evaporated on a RE. The residue is dissolved with EtOAc and water, the water phase separated, extracted twice with EtOAc and discarded. The organic phases are washed with water, extracted with 200 ml of 1N HCl and 2 portions of 200 ml 0.5 N HCl, washed with saturated $Na_2CO_3$ solution and brine, dried ($Na_2SO_4$) and concentrated by evaporation. Column chromatography ($SiO_2$, hexane/EtOAc 1:1→1:2) and recrystallisation from acetonitrile yield rac. 4-[1-(6-methoxy-pyridin-3-yl)-methylidene]-3-methyl-3,4-dihydro-2H-isoquinolin-1-one (m.p. 194–195° C.; FAB-MS: $(M+H)^+$=281; TLC(hexane/EtOAc 1:1): $R_f$=0.26). The acidic aqueous extracts are collected in a solution of 60 g of $K_2CO_3$ in 0.5 l of water. Upon standing, 4-[(6-methoxy-pyridin-3-yl)-methyl]-3-methyl-2H-isoquinolin-1-one crystallises, and can be filtered off by suction, washed with water and recrystallised from boiling EtOAc/methanol (m.p. 234–236° C.; FAB-MS: $(M+H)^+$=281; TLC(hexane/EtOAc 1:1): $R_f$=0.18).

Step 45.5: 4-[(6-methoxy-pyridin-3-yl)-methyl]-3-methyl-2H-isoquinolin-1-one is converted to 1-chloro-4-[(6-methoxy-pyridin-3-yl)-methyl]-3-methylisoquinoline (contaminated with 1-chloro-4-[(6-chloro-pyridin-3-yl)-methyl]-3-methylisoquinoline) in analogous manner to example 1.6: FAB-MS: $(M+H)^+$=299.

Examples 46, 47 and 48

The following compounds of formula II-In are obtained analogously to example 45:

R = Cl: (Il)
R = OMe: (Im)
R = OH: (In)

| Ex. | Y—NH | R | HPLC grad$_{20-100}$ | FAB-MS $(M+H)^+$ | m.p. [° C.] |
|---|---|---|---|---|---|
| 46a 47a | (4-methyl-3-bromophenyl)NH | OMe OH | | | |
| 46b 47b | (4-tert-butyl-3-bromophenyl)NH | OMe OH | | | |
| 46c 47c 48c | (4-chloro-3-trifluoromethylphenyl)NH | OMe OH Cl | 12.1 10.1 13.0 | 458 444 462 | 154–156 |

-continued

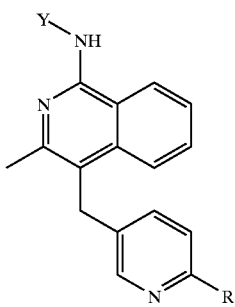

R = Cl: (Il)
R = OMe: (Im)
R = OH: (In)

| Ex. | Y—NH | R | HPLC grad$_{20-100}$ | FAB-MS (M + H)$^+$ | m.p. [° C.] |
|---|---|---|---|---|---|
| 46d | | OMe | | | |
| 47d | | OH | | | |
| 46e | | OMe | 12.4 | 412 | 122–123 |
| 47e* | | OH | 10.4 | 398 | |
| 48e | | Cl | 13.3 | 416 | |
| 46f | | OMe | 11.4 | 442 | |
| 47f | | OH | 9.5 | 428 | |
| 48f | | Cl | 12.4 | 446 | |
| 46g** | | OMe | | | |
| 47g* | | OH | | | |
| 46h | | OMe | 12.2 | 462/464 | |
| 47h | | OH | 10.1 | 448/450 | 198–200 |

*Prepared by demethylation (1. Me$_3$SiI/CHCl$_3$, 2. hydrolysis) from the 6-methoxy-pyridine derivative
**Prepared analogously to example 19

Example 49

In a sealed glass bottle under N$_2$-atmosphere, 424 mg (2.92 mmol) of trans 2-isopropyl-[1,3]dioxan-5-ylamine, 396 mg (1.46 mmol) of 1-chloro-4-[(6-hydroxy-pyridin-3-yl)methyl]-isoquinoline (contains 1-iodo derivative) and 2 ml of tributylamine are stirred at 150° C. for 48 h. The resulting mixture is diluted with EtOAc and NaHCO$_3$-solution, the aqueous layer is separated and extracted twice with EtOAc. The organic phases are washed with brine, dried (Na$_2$SO$_4$) and concentrated in vaccuo. "Reversed Phase" medium-pressure chromatography (water/acetonitrile/TFA) yields trans 1-(2-isopropyl-[1,3]dioxan-5-ylamino)-4-[(6-hydroxy-pyridin-3-yl)methyl]-isoquinoline; FAB-MS; (M+H)$^+$=286; HPLC(gradient$_{20-100}$) t$_{Ret}$=8.6.

The starting material is prepared as follows:

Step 49.1: Under exclusion of moisture, to 500 mg (1.76 mmol) of 1-chloro-4-[(6-methoxy-pyridin-3-yl)methyl]-isoquinoline (step 28.6) in 9 ml of chloroform, 488 μl (3.58 mmol) of Me$_3$SiI are added. Then the mixture is stirred for 8 h at 60° C. Dilution of the mixture with EtOAc and NaHCO$_3$-solution, stirring and filtration of the suspension yields 1-chloro-4-[(6-hydroxy-pyridin-3-yl)methyl]-isoquinoline, contaminated with 1-iodo-4-[(6-hydroxy-pyridin-3-yl)methyl]-isoquinoline; FAB-MS: (M+H)$^+$=271$^{chloride}$/363$^{iodide}$; HPLC(gradient$_{20-100}$) t$_{Ret}$=10.2$^{chloride}$/10.8$^{iodide}$. From the filtrate, more product can be obtained by extraction with EtOAc.

Step 49.2: To an ice-cold solution of 5.4 g (59 mmol) of 2-amino-1,3-propandiol in 50 ml of THF and 5 ml of water, 11.7 g (85 mmol) of K$_2$CO$_3$ and 10.5 ml (95% purity; 71 mmol) of benzyl chloroformate are added. After stirring for 1 h at 0° C. and 15 h at RT, the mixture is diluted with EtOAc. After drying by addition of solid Na$_2$SO$_4$, filtration, washing with EtOAc and partial concentration in vaccuo, the product starts to crystallise. Filtration and washing with hexane yield 2-benzyloxy-carbonylamino-1,3-propandiol; m.p. 108–109° C.; FAB-MS: (M+H)$^+$=226.

Step 49.3: A solution of 10.1 g (44.8 mmol) of 2-benzyloxy-carbonylamino-1,3-propandiol, 123 mg of p-toluene-sulfonic acid and 4.2 ml (46 mmol) of isobutyraldehyde in 100 ml of benzene is heated at reflux temperature in a water separating equipment. After 5 h, another portion of 4.2 ml of isobutyraldehyde is added and heating is continued for totally 16 h. Upon cooling to RT, trans (2-isopropyl-[1,3]dioxan-5-yl)-carbaminic acid benzylester crystallises in plates; m.p. 152° C.; FAB-MS: (M+H)$^+$=226. More product can be obtained from the filtrate by washing it with NaHCO$_3$ solution, water and brine, drying (Na$_2$SO$_4$), concentration in vaccuo and recrystallisation from boiling toluene.

Step 49.4: Hydrogenation of 4.07 g (14.6 mmol) of trans (2-isopropyl-[1,3]dioxan-5-yl)-carbaminic acid benzylester in 80 ml of EtOAc in the presence of 0.4 g of Pd/C (10%), followed by filtration through Celite and concentration in vaccuo, yields trans 2-isopropyl-[1,3]dioxan-5-ylamine; $^1$H NMR (CDCl$_3$) δ4.11 (m, 3H), 3.20 (t, 10.5 Hz, 2H), 3.04 (m, 1H), 1.80 (m, 1H), 1.56 (sb, H$_2$N), 0.93 (d, 6H).

Example 50

Test for activity against KDR VEGF-receptor tyrosine kinase The test is conducted using KDR VEGF-receptor tyrosine kinase, as described hereinabove. The IC$_{50}$ values determined are given below, insofar as they have been accurately recorded:

| Compound from Example | IC$_{50}$ (μmol) |
|---|---|
| 1 | 0.105 |
| 2 | 0.049 |
| 3 | 0.123 |
| 5 | 0.025 |
| 7 | 0.185 |
| 8 | 0.027 |

| Compound from Example | IC$_{50}$ ($\mu$mol) |
| --- | --- |
| 9 | 0.004 |
| 10 | 0.033 |
| 11 | 0.041 |
| 12 | 0.192 |
| 13 | 0.053 |
| 16 (E isomer) | 0.196 |
| 17 (E isomer) | 0.072 |
| 29 (E isomer) | 0.087 |
| 19 | 0.127 |
| 20 | 0.048 |
| 21 | 0.015 |
| 34g | 0.137 |
| 37b | 0.092 |
| 40e | 0.081 |

Example 51

Test for activity against VEGF-induced KDR phosphorylation The cellular in vitro test is carried out using VEGF and KDR-transfected cells, as described above. The ED$_{50}$ values determined are given below, insofar as they have been accurately recorded:

| Compound from Example | ED$_{50}$ ($\mu$mol) |
| --- | --- |
| 5 | 0.010 |
| 8 | 0.011 |
| 9 | 0.091 |
| 33e | 0.028 |
| 34e | 0.019 |
| 34g | 0.029 |
| 40e | 0.052 |
| 41e | 0.022 |

Example 52

Soft Capsules 5000 soft gelatin capsules, each comprising as active ingredient 0.05 g of one of the compounds of formula I mentioned in the preceding Examples, are prepared as follows:

| Composition | |
| --- | --- |
| active ingredient | 250 g |
| Lauroglykol | 2 litres |

Preparation process: The pulverized active ingredient is suspended in Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

What is claimed is:
1. A compound of formula I:

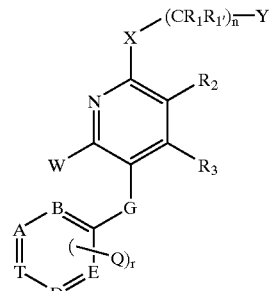

wherein
A or D is N, while the other is CH, and T is CH or CR$_4$;
or T is N and A or D is CH, while the other is CR$_4$ and, with the proviso that at least one of A and D is CR$_4$ when T is N;
R$_4$ is lower alkyl, lower alkenyl, lower alkylthio, mercapto, free, etherified or esterified hydroxy, unsubstituted, mono- or disubstituted amino or halogen;
B and E, independently of one another, are each N or CH;
G is C$_1$–C$_6$-alkylene, C$_2$–C$_6$-alkenylene, or hydroxy-substituted C$_1$–C$_6$-alkylene or C$_3$–C$_6$-alkenylene,
n is 0 to 2;
Q is lower alkyl, whereby A, D and T are not substituted by Q if they represent CR$_4$;
r is 0 to 5;
R$_1$ und R$_{1'}$ independently of one another are each hydrogen or lower alkyl;
R$_2$ and R$_3$
a) independently of one another, are each lower alkyl; or
b) together form a bridge of the part formula I*;

wherein the ring members T$_1$, T$_2$, T$_3$ and T$_4$, independently of one another, are each nitrogen or CH, and binding is achieved via the atoms T$_1$ and T$_4$, the bonds indicated by a wavy line, independently of one another, are each either single or double bonds, m is 0 to 4 and Z is a substituent of one or more carbon atoms, whereby Z is unsubstituted, mono- or disubstituted amino, halogen, unsubstituted or substituted alkyl, free, etherified or esterified hydroxy, nitro, cyano, free or esterified carboxy, alkanoyl, unsubstituted, N-mono- or N,N-disubstituted carbamoyl, amidino, guanidino, mercapto, sulfo, phenylthio, phenyl lower alkylthio, alkylphenylthio, phenylsulfinyl, phenyl lower alkylsulfinyl, alkylphenylsulfinyl, phenylsulfonyl, phenyl lower alkylsulfonyl or alkylphenylsulfonyl, whereby if more than 1 radical Z is present (m≧2), the substituents Z are identical or different;

W is hydrogen,

X is —N(R$_5$); and

R$_5$ is H or lower alkyl;

and Y is hydrogen, aryl, which is unsubstituted or substituted by one or more substituents, heterocyclyl, which is unsubstituted or substituted by one or more substituents or unsubstituted or substituted cycloalkyl;

or a tautomer of the said compound;

or an N-oxide of the said compound or tautomers thereof, whereby one or more N atoms carry an oxygen atom;

or a salt of the said compounds.

2. A compound of formula I according to claim 1, wherein A or D is N, while the other is CH, and T is CH or CR$_4$; or T is N and A or D is CH, while the other is CR$_4$ and, with the proviso that A or D is CR$_4$ when T is N;

Y is hydrogen, aryl, which is unsubstituted or substituted by one or more substituents, heteroaryl, which is unsubstituted or substituted by one or more substituents, or unsubstituted or substituted cycloalkyl;

and the remaining substituents and symbols are defined as in claim 1;

or a tautomer of the said compound;

or an N-oxide of the said compound or tautomers thereof, whereby one or more N atoms carry an oxygen atom;

or a salt of the said compounds.

3. A compound of formula I according to claim 1, wherein A or D is N, while the other is CH, and T is CH or CR$_4$; or T is N and A or D is CH, while the other is CR$_4$ and, with the proviso that A or D is CR$_4$ when T is N;

R$_4$ is lower alkyl, lower alkenyl, lower alkylthio, mercapto, hydroxy, lower alkoxy, phenyl lower alkoxy, phenyloxy, halogen lower alkoxy, lower alkanoyloxy, lower alkoxycarbonyloxy, phenyl lower alkoxycarbonyloxy, amino, N-lower alkylamino, hydroxy lower alkylamino, lower alkanoylamino, phenyl lower alkylamino, N,N-di-lower alkylamino oder halogen;

B and E, independently of one another, are each N or CH;

G is C$_1$–C$_6$-alkylene, C$_2$–C$_6$-alkenylene; C$_1$–C$_8$-alkylene or C$_3$–C$_6$-alkenylene substituted by hydroxy or by lower alkanoyloxy;

n is 0 to 2;

Q is lower alkyl, whereby A, D and T are not substituted by Q if they represent CR$_4$;

r is 0 to 5;

R$_1$ and R$_1$, independently of one another are each hydrogen or lower alkyl;

R$_2$ and R$_3$
a) independently of one another, are each lower alkyl; or
b) together form a bridge of part formula I*, wherein at most two of the ring members T$_1$, T$_2$, T$_3$ and T$_4$ are nitrogen, and the others are CH, and binding is achieved via the atoms T$_1$ and T$_4$, the bonds indicated by a wavy line, independently of one another, are each either single or double bonds, m is 0 to 4 and Z is a substituent of one or more carbon atoms, whereby Z is lower alkyl, amino, N-lower alkylamino, hydroxy lower alkylamino, lower alkanoylamino, N,N-di-lower alkylamino, halogen, halogen lower alkyl, hydroxy, lower alkoxy, halogen lower alkoxy, lower alkanoyloxy, lower alkoxycarbonyloxy, nitro, cyano, carboxy, lower alkoxycarbonyl, lower alkanoyl, carbamoyl; carbamoyl substituted on nitrogen by one or two substituents selected independently of one another from the group consisting of lower alkyl and hydroxy lower alkyl; amidino, guanidine, mercapto or sulfo, whereby if more than one radical Z is present (m≧2), the substituents Z are identical or different;

W is hydrogen,

X is —N(R$_5$); and

R$_5$ is H or lower alkyl;

and Y is unsubstituted or substituted cyclohexyl, isoquinolyl or unsubstituted or substituted phenyl, whereby substituted cyclohexyl and substituted phenyl are substituted by one or more substituents selected independently of one another from the group consisting of lower alkyl, lower alkoxy, halogen and halogen lower alkyl;

or a tautomer of the said compound;

or an N-oxide of the said compound or tautomers thereof, whereby one or more N atoms carry an oxygen atom;

or a salt of the said compounds.

4. A compound of formula I according to claim 1, wherein A or D is N, while the other is CH, and T is CH or CR$_4$; or A or D is CH, while the other is CR$_4$, and T is N;

R$_4$ is lower alkyl, lower alkenyl, lower alkylthio, mercapto, hydroxy, lower alkoxy, halogen lower alkoxy, lower alkanoyloxy, lower alkoxycarbonyloxy, amino, N-lower alkylamino, hydroxy lower alkylamino, lower alkanoylamino, N,N-di-lower alkylamino or halogen;

B and E are CH;

G is C$_1$–C$_6$-alkylene, C$_2$–C$_6$alkenylene; C$_1$–C$_6$-alkylene or C$_3$–C$_6$-alkenylene substituted by hydroxy or by lower alkanoyloxy;

n is 0 to 2;

Q is lower alkyl, whereby A, D and T are not substituted by Q If they represent CR$_4$;

r is 0 or 1;

R$_1$ und R$_1$, independently of one another are each hydrogen or lower alkyl;

R$_2$ and R$_3$ together form a bridge of part formula I*, wherein the ring members T$_1$, T$_2$, T$_3$ and T$_4$ are CH, and binding is achieved via the atoms T$_1$ and T$_4$, the bonds indicated by a wavy line are double bonds, m is 0 to 2 and Z is a substituent of one or more carbon atoms, whereby Z is lower alkyl, amino, N-lower alkylamino, hydroxy lower alkylamino, lower alkanoylamino, N,N-di-lower alkylamino, halogen, halogen lower alkyl, hydroxy, lower alkoxy, halogen lower alkoxy, lower alkanoyloxy, lower alkoxycarbonyloxy, nitro, cyano, carboxy, lower alkoxycarbonyl, lower alkanoyl, carbamoyl; carbamoyl substituted on nitrogen by one or two substituents selected independently of one another from the group consisting of lower alkyl and hydroxy lower alkyl; amidino, guanidino, mercapto or sulfo, whereby if more than one radical Z is present (m=2), the substituents Z are identical or different;

W is hydrogen;

X is —N(R$_5$)—; and

R$_5$ is H or lower alkyl;

and Y is unsubstituted or substituted cyclohexyl, isoquinolyl or unsubstituted or substituted phenyl, whereby substituted cyclohexyl and substituted phenyl are substituted by one or more substituents selected independently of one another from the group consisting of lower alkyl, lower alkoxy, halogen and halogen lower alkyl;

or a tautomer of the said compound;

or an N-oxide of the said compound or tautomers thereof, whereby one or more N atoms carry an oxygen atom;

or a salt of the said compounds.

5. A compound of formula I according to claim 1, wherein

A or D is N, while the other is CH, and T is CH or $CR_4$; or

A or D is CH, while the other is $CR_4$, and T is N;

$R_4$ is lower alkyl, hydroxy, lower alkoxy or halogen;

B and E are CH;

G is $C_1$–$C_6$-alkylene, $C_2$–$C_6$-alkenylene; $C_1$–$C_8$-alkylene or $C_3$–$C_6$-alkenylene substituted by hydroxy or by lower alkanoyloxy;

n is 0 to 2;

r is 0;

$R_1$ und $R_1'$ independently of one another are each hydrogen or lower alkyl;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds indicated by a wavy line are double bonds, and m is 0;

W stands for hydrogen;

X is —$N(R_5)$—; and $R_5$ is H or lower alkyl;

and Y is substituted cyclohexyl, isoquinolyl or unsubstituted or substituted phenyl, whereby substituted cyclohexyl and substituted phenyl are substituted by one to three substituents selected independently of one another from the group consisting of lower alkyl, lower alkoxy, halogen and halogen lower alkyl;

or a tautomer of the said compound;

or an N-oxide of the said compound or tautomers thereof, whereby one or more N atoms carry an oxygen atom;

or a salt of the said compounds.

6. A compound of formula I according to claim 1, wherein

A or D is N, while the other is CH, and T is CH or $CR_4$; or

A or D is CH, while the other is $CR_4$, and T is N;

$R_4$ is lower alkyl, hydroxy, lower alkoxy or halogen;

B and E are CH;

G is $C_1$–$C_6$-alkylene or $C_2$–$C_6$-alkenylene;

n is 0 or 1;

r is 0;

$R_1$ und $R_1'$ independently of one another are each hydrogen or lower alkyl;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds indicated by a wavy line are double bonds, and m is 0;

W stands for hydrogen;

X is —$N(R_5)$—; and $R_5$ is H or lower alkyl;

and Y is substituted cyclohexyl, isoquinolyl or unsubstituted or substituted phenyl, whereby substituted cyclohexyl and substituted phenyl are substituted by one to three substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

7. A compound of formula I according to claim 1, wherein

A or D is N, while the other is CH, and T is CH or $CR_4$; or

A or D is CH, while the other is $CR_4$, and T is N;

$R_4$ is methyl, hydroxy or methoxy;

B and E are CH;

G is methylene, ethylene or ethenylene;

n is 0;

r is 0;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds indicated by a wavy line are double bonds, and m is 0;

W is hydrogen;

X is —$N(R_5)$—; and $R_5$ is H;

and Y is substituted cyclohexyl, isoquinolyl or unsubstituted or substituted phenyl, whereby substituted cyclohexyl and substituted phenyl are substituted by one or two substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

8. A compound of formula I according to claim 1, wherein

A or D is N, while the other is CH, and T is CH or $CR_4$; or

A or D is CH, while the other is $CR_4$, and T is N;

$R_4$ is methyl, hydroxy or methoxy;

B and E are CH;

G is methylene, ethylene or ethenylene;

n is 0;

r is 0;

$R_2$ and $R_3$ together form a bridge of part formula I*, in which the ring members $T_1$, $T_2$, $T_3$ and $T_4$ are CH and binding is achieved via the atoms $T_1$ and $T_4$, the bonds indicated by a wavy line are double bonds, and m is 0;

W is hydrogen;

X is —$N(R_5)$—; and $R_5$ is H;

and Y is substituted cyclohexyl, isoquinolyl or unsubstituted or substituted phenyl, whereby substituted cyclohexyl is substituted by one or two independent substituents lower alkyl and substituted phenyl is substituted by one or two substituents selected independently of one another from the group consisting of lower alkyl, halogen and halogen lower alkyl;

or a tautomer of the said compound;

or an N-oxide of the said compound or tautomers thereof, whereby one or more N atoms carry an oxygen atom;

or a salt of the said compounds.

9. A compound of formula I according to claim 1, wherein
A or D is N, while the other is CH, and T is CH or $CR_4$;
$R_4$ is methyl, hydroxy, methoxy or halogen;
B and E are CH;
G is methylene, ethylene or ethenylene;
n 0;
r is 0;
$R_2$ and $R_3$ together form a bridge of part formula I*, in which 0 to 2 of the ring members $T_1$, $T_2$, $T_3$ and $T_4$ are nitrogen and the remaining ring members are CH, and binding is achieved via the atoms $T_1$ and $T_4$, the bonds indicated by a wavy line are double bonds, and m is 0;
W is hydrogen;
X is —$N(R_5)$—; and
$R_5$ is H;
and Y is substituted cyclohexyl, isoquinolyl or unsubstituted or substituted phenyl, whereby substituted cyclohexyl and substituted phenyl are substituted by one or two substituents selected independently of one another from the group consisting of lower alkyl, halogen and halogen lower alkyl;
or a tautomer of the said compound;
or an N-oxide of the said compound or tautomers thereof, whereby one or more N atoms carry an oxygen atom;
or a salt of the said compounds.

10. A compound of formula I according to claim 9, wherein
$R_4$ is methyl, hydroxy or methoxy;
$R_2$ and $R_3$ together form a bridge of part formula I* in which the ring members $T_1$, $T_2$, $T_3$ and $T_4$ are CH and binding is achieved via the atoms $T_1$ and $T_4$, the bonds indicated by a wavy line are double bonds, end m is 0;
W is hydrogen;
or a tautomer of the said compound;
or an N-oxide of the said compound or tautomers thereof, whereby one or more N atoms carry an oxygen atom;
or a salt of the said compounds.

11. A compound of formula I according to claim 1, wherein
A or D is CH, while the other is $CR_4$, and T is N;
$R_4$ is methyl, hydroxy, methoxy or halogen;
B and E are CH;
G is methylene, ethylene or ethenylene;
n is 0;
r is 0;
$R_2$ and $R_3$ together form a bridge of part formula I*, in which the ring members $T_1$, $T_2$, $T_3$ and $T_4$ are CH and binding is achieved via the atoms $T_1$ and $T_4$, the bonds indicated by a wavy line are double bonds, and m is 0;
W is hydrogen;
X is —$N(R_5)$—; and
$R_5$ is H;
and Y is substituted cyclohexyl, isoquinolyl or unsubstituted or substituted phenyl, whereby substituted cyclohexyl and substituted phenyl are substituted by one or two substituents selected independently of one another from the group consisting of lower alkyl, halogen and halogen lower alkyl;
or a tautomer of the said compound;
or an N-oxide of the said compound or tautomers thereof, whereby one or more N atoms carry an oxygen atom;
or a salt of the said compounds.

12. A compound of formula I according to claim 11, wherein
$R_4$ is methyl, hydroxy or methoxy;
or a tautomer of the said compound;
or an N-oxide of the said compound or tautomers thereof, whereby one or more N atoms carry an oxygen atom;
or a salt of the said compounds.

13. A compound of formula I according to claim 1, selected from the group consisting of
1-(4-chloroanilino)-4-[2-(pyridin-3-yl)-ethyl]-isoquinoline;
(Z)-1-(3-bromo-4-methylanilino)-4-[2-(pyridin-3-yl)-vinyl]-isoquinoline;
(E)-1-(3-bromo-4-methylanilino)-4-[2-(pyridin-3-yl)-vinyl]-isoquinoline;
1-(3-bromo-4-methylanilino)-4-[2-(pyridin-3-yl)-ethyl]-isoquinoline;
1-[4(tert-butyl)-anilino]-4-[2-(pyridin-3-yl)-ethyl]-isoquinoline;
1-(3-trfluoromethylanilino)-4-[2-(pyridin-3-yl)-ethyl]-isoquinoline;
1-(3-chloro-5-trfluoromethylanilino)-4-[2-(pyridin-3-yl)-ethyl]-isoquinoline;
1-(4-isopropyl-3-methylanilino)-4-[2-(pyridin-3-yl)-ethyl]-isoquinoline;
1-(3-bromo-4-ethylanilino)-4-[2-(pyridin-3-yl)-ethyl]-isoquinoline;
1-[3-(tert-butyl)-anilino]-4-[2-(pyridin-3-yl)-ethyl]-isoquinoline;
1-[3,4-bis(trifluoromethyl)-anilino]-4-[2-(pyridin-3-yl)-ethyl]-isoquinoline;
1-[3,5-bis(trifluoromethyl)-anilino]-4-[2-(pyridin-3-yl)-ethyl]-isoquinoline;
1-(4-chloro-3-trifluoromethylanilino)-4-[2-(pyridin-3-yl)-ethyl]-isoquinoline;
1-(3-bromo-5-trifluoromethylanilino)-4-[2-(pyridin-3-yl)-ethyl]-isoquinoline;
1-anilino-4-[2-(pyridin-3-yl)-ethyl]-isoquinoline;
cis 1-[4-(tert-butyl)-cyclohexylamino]-4-[2-(pyridin-3-yl)-ethyl]-isoquinoline;
trans 1-[4-(tert-butyl)-cyclohexylamino]-4-[2-(pyridin-3-yl)-ethyl]-isoquinoline;
cis 1-[4-isopropyl-cyclohexylamino]-4-[2-(pyridin-3-yl)-ethyl]-isoquinoline;
trans 1-[4-isopropyl-cyclohexylamino]-4-[2-(pyridin-3-yl)-ethyl]-isoquinoline;
cis 1-(4-ethyl-cyclohexylamino)-4-[2-(pyridin-3-yl)-ethyl]-isoquinoline;
trans 1-(4-ethyl-cyclohexylamino)-4-[2-(pyridin-3-yl)-ethyl]-isoquinoline;
trans 1-(4-isopropyl-cyclohexylamino)-4-[2-(6-methyl-pyridin-3-yl)-ethyl]-isoquinoline;
1-(4-isopropyl-3-methylanilino)-4-[2-(6-methyl-pyridin-3-yl)-ethyl]-isoquinoline;
1-(3-bromo-4-ethylanilino)-4-[2-(6-methyl-pyridin-3-yl)-ethyl]-isoquinoline;
1-(3-chloro-5-trfluoromethylanilino)-4-[2-(6-methyl-pyridin-3-yl)-ethyl]-isoquinoline;
1-(4-propylanilino)-4-[2-(6-methyl-pyridin-3-yl)-ethyl]-isoquinoline;

1-(3-trifluoromethyl-4-propylanilino)-4-[2-(6-methyl-pyridin-3-yl)-ethyl]-isoquinoline;
1-(3-trifluoromethylanilino)-4-[2-(6-methyl-pyridin-3-yl)-ethyl]-isoquinoline;
trans 1-(4-isopropyl-cyclohexylamino)-4-[2-(2-methoxy-pyridin-4-yl)-ethyl]-isoquinoline;
trans 1-(4-isopropyl-cyclohexylamino)-4-[2-(2-hydroxy-pyridin-4-yl)-ethyl]-isoquinoline;
trans 1-(4-isopropyl-cyclohexylamino)-4-[(6-methoxy-pyridin-3-yl)-methyl]-isoquinoline;
trans 1-(4-isopropyl-cyclohexylamino)-4-[(6-hydroxy-pyridin-3-yl)-methyl]-isoquinoline;
1-(4-isopropyl-3-methylcyclohexyl-amino)-4-[(6-methoxy-pyridin-3-yl)-methyl]-isoquinoline;
1-(4-isopropyl-3-methylcyclohexyl-amino)-4-[(6-hydroxy-pyridin-3-yl)-methyl]-isoquinoline;
1-(isoquinolin-3-yl)-4-[2-(6-methoxy-pyridin-3-yl)-ethyl]-isoquinoline;
1-(isoquinolin-3-yl)-4-[2-(6-hydroxy-pyridin-3-yl)-ethyl]-isoquinoline;
1-(3-bromo-4-ethylanilino)-4-[2-(2-methoxy-pyridin-4-yl)-ethyl]-isoquinoline;
1-(4-isopropyl-3-methylanilino)-4-[2-(2-methoxy-pyridin-4-yl)-ethyl]-isoquinoline;
1-(3-chloro-5-trifluoromethylanilino)-4-[2-(2-methoxy-pyridin-4-yl)-ethyl]-isoquinoline;
1-(3-trifluoromethylanilino)-4-[2-(2-methoxy-pyridin-4-yl)-ethyl]-isoquinoline;
1-(3-bromo-4-ethylanilino)-4-[2-(2-hydroxy-pyridin-4-yl)-ethyl]-isoquinoline;
1-(4-isopropyl-3-methylanilino)-4-[2-(2-hydroxy-pyridin-4-yl)ethyl]-isoquinoline;
1-(3-chloro-5-trifluoromethylanilino)-4-[2-(2-hydroxy-pyridin-4-yl)-ethyl]-isoquinoline;
1-(3-trifluoromethylanilino)-4-[2-(2-hydroxy-pyridin-4-yl)-ethyl]-[isoquinoline;
1-(3-bromo-4-methylanilino)-4-[(6-methoxy-pyridin-3-yl)-methyl]-isoquinoline;
1-[3-bromo-4-(tert-butyl)-anilino]-4-[(6-methoxy-pyridin-3-yl)-methyl]-isoquinoline;
1-(3-fluoro-5-trifluoromethylanilino)-4-[(6-methoxy-pyridin-3-yl)-methyl]-isoquinoline;
1-[3,4-bis(trifluoromethyl)-anilino]-4-[(6-methoxy-pyridin-3-yl)-methyl]-isoquinoline;
1-(3-bromo-4-methylanilino)-4-[(6-hydroxy-pyridin-3-yl)-methyl]-isoquinoline;
1-[3-bromo4-(tert-butyl)-anilino]-4-[(6-hydroxy-pyridin-3-yl)-methyl]-isoquinoline;
1-(3-fluoro-5-trifluoromethylanilino)-4-[(6-hydroxy-pyridin-3-yl)-methyl]-isoquinoline;
1-[3,4-bis(trifluoromethyl)-anilino]-4-[(6-hydroxy-pyridin-3-yl)-methyl]-isoquinoline;
and pharmaceutically acceptable salts thereof.

14. 1-(4-(tert-butyl)-anilino]-4-[2-(pyridin-3-yl)-ethyl]-isoquinoline of formula I according to claim 1, or a pharmaceutically acceptable salt thereof.

15. 1-[4-isopropyl-3-methylanilino]-4-[2-(pyridin-3-yl)-ethyl]-isoquinoline of formula I according to claim 1, or a pharmaceutically acceptable salt thereof.

16. A compound of formula I according to claim 1, selected from the group consisting of
1-[4-(tert-butyl)-anilino]-4-[(6-hydroxy-pyridin-3-yl)-methyl]-isoquinoline;

5-[4-(tert-butyl)-anilino]-8-[(6-hydroxy-pyridin-3-yl)-methyl]-[1,6]naphthyridine;
1-[4-(tert-butyl)-anilino]-4-[(6-methoxy-pyridin-3-yl)-methyl]-isoquinoline;
1-(3-bromo-4-ethylanilino)-4-[(6-hydroxy-pyridin-3-yl)-methyl]-isoquinoline;
5-[4-(tert-butyl)-anilino]-8-[(6-methoxy-pyridin-3-yl)-methyl]-[1,6]naphthyridine;
and pharmaceutically acceptable salts thereof.

17. A pharmaceutical composition comprising a compound of formula I or a pharmaceutically acceptable salt thereof according to claim 1, together with at least one pharmaceutically acceptable carrier.

18. A method for the treatment of a disease which responds to an inhibition of angiogenesis comprising administering a compound of formula I according to claim 1 or a pharmaceutically acceptable salt thereof.

19. A method for the treatment of a disease which responds to an inhibition of VEGF-receptor tyrosine kinase comprising administering a compound of formula I according to claim 1, or a pharmaceutically acceptable salt thereof.

20. A process for the preparation of a compound of formula I according to claim 1, or a tautomer of a compound of formula I, or a N-oxide of a compound of formula I or the tautomers thereof, whereby one or more N-atoms, carry an oxygen atom, or a salt of the said compounds, in which process (a) in order to prepare a compound of formula I, in which G has the significance $C_2-C_6$-alkylene, $C_2-C_6$-alkenylene; or $C_2-C_6$-alkylene or $C_3-C_6$-alkenylene substituted by acyloxy or hydroxy; a compound of formula IV;

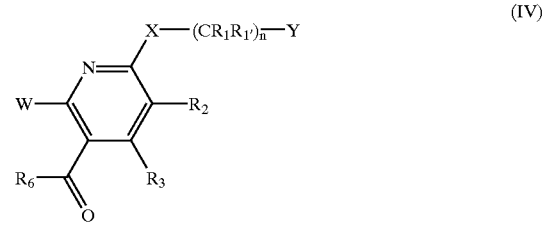

(IV)

wherein n, $R_1$, $R_{1'}$, X, Y, W, $R_2$ and $R_3$ are as described for a compound of formula I, and $R_6$ is H or $C_1-C_4$-alkyl, is reacted in the presence of a base with a compound of formula V:

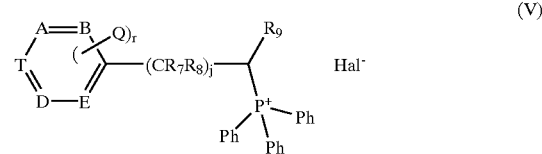

(V)

wherein r, A, B, D, E, T and Q are defined as for a compound of formula I, $R_7$, $R_8$ and $R_9$ independently of one another are H or $C_1-C_4$-alkyl, j is an integer between 0 and 4, Hal⁻ is a halide end Ph signifies phenyl, and the compound of formula I thus obtained, with G=—$CR_6$=$CR_9$—$(CR_7R_8)_j$— is converted, if desired, into another compound of formula I, by hydrogenation under catalysis with a secondary group metal or by addition of water and optional subsequent acylation, or (b) in order to prepare a compound of formula I, wherein G is methylene (—CH$_2$—), a compound of formula VII:

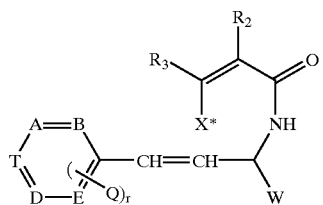

(VII)

wherein r, A, B, D, E, T, W, Q, R$_2$ and R$_3$ are defined as for a compound of formula I, X* is bromine, iodine or trifluoromethylsulfonyloxy, and the double bond —CH=CH— is present in cis- or in tans-form, is reacted with palladium diacetate, and the compound of formula II* thus obtained:

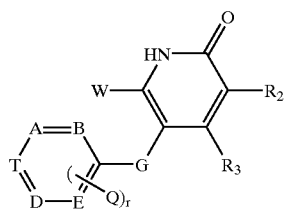

(II*)

in which G is methylene, is reacted by introducing a nucleofugal group to form a compound of formula II, in which G is methylene, whereby the further reaction to form a compound of formula I is carried out as described above under a);

whereby functional groups which are present in the starting compounds of processes a to f and are not intended to take part in the reaction, are present in protected form if necessary, and protecting groups that are present are cleaved, whereby the said staffing compounds may also exist in the form of salts provided that a salt-forming group is present and a reaction in salt form is possible;

and, if so desired, an obtainable compound of formula I or an N-oxide thereof is converted into another compound of formula I or an N-oxide thereof, a free compound of formula I or an N-oxide thereof is converted into a salt an obtainable salt of a compound of formula I or an N-oxide thereof is converted into the free compound or another salt, and/or a mixture of isomeric compounds of formula I or N-oxides thereof is separated into the individual isomers.

* * * * *

UNITED STATES PATENT AND TRADEMARK OFFICE
CERTIFICATE OF CORRECTION

PATENT NO. : 6,706,731 B2
APPLICATION NO. : 10/203579
DATED : March 16, 2004
INVENTOR(S) : Bold et al.

It is certified that error appears in the above-identified patent and that said Letters Patent is hereby corrected as shown below:

Column 61
 Line 43, change "$C_1$-$C_8$-alkylene" to -- $C_1$-$C_6$-alkylene --.

Column 63
 Line 20, change "$C_1$-$C_8$-alkylene" to -- $C_1$-$C_6$-alkylene --.

Column 69
 Line 18, change "tans-form" to -- trans-form --.

Signed and Sealed this

Third Day of April, 2007

JON W. DUDAS
*Director of the United States Patent and Trademark Office*